United States Patent
Friebe et al.

(10) Patent No.: US 12,318,254 B2
(45) Date of Patent: Jun. 3, 2025

(54) METHOD AND DEVICE FOR CHARACTERIZING AT LEAST ONE OBJECT DEPICTED IN AN ULTRASOUND IMAGE

(71) Applicant: Brainlab AG, Munich (DE)

(72) Inventors: Michael Friebe, Munich (DE); Nazila Esmaeili, Munich (DE); Elmer Jeto Gomes Ataide, Munich (DE); Prabal Poudel, Munich (DE); Alfredo Illanes, Munich (DE); Jens Ziegle, Munich (DE); Satish Balakrishnan, Munich (DE)

(73) Assignee: Brainlab AG, Munich (DE)

( * ) Notice: Subject to any disclaimer, the term of this patent is extended or adjusted under 35 U.S.C. 154(b) by 119 days.

(21) Appl. No.: 18/014,837

(22) PCT Filed: Jul. 2, 2021

(86) PCT No.: PCT/EP2021/068351
§ 371 (c)(1),
(2) Date: Jan. 6, 2023

(87) PCT Pub. No.: WO2022/008376
PCT Pub. Date: Jan. 13, 2022

(65) Prior Publication Data
US 2023/0270414 A1    Aug. 31, 2023

(30) Foreign Application Priority Data

Jul. 9, 2020  (DE) ..................... 10 2020 118 132.9
Jul. 9, 2020  (DE) ..................... 10 2020 118 133.7

(51) Int. Cl.
A61B 8/00     (2006.01)
G06T 7/00     (2017.01)
(Continued)

(52) U.S. Cl.
CPC .......... *A61B 8/5207* (2013.01); *G06T 7/0012* (2013.01); *G06T 7/13* (2017.01);
(Continued)

(58) Field of Classification Search
None
See application file for complete search history.

(56) References Cited

U.S. PATENT DOCUMENTS 5,528,302 A      6/1996  Basoglu et al.
2003/0199762 A1*  10/2003 Fritz ..................... G06T 7/60
                                                         600/437

(Continued)

OTHER PUBLICATIONS

Poudel et al., "Thyroid Ultrasound Texture Classification Using Autoregressive Features in Conjunction With Machine Learning Approaches," (Jun. 17, 2019), IEEE Access ( vol. 7), p. 79354-79365. (Year: 2019).*

(Continued)

*Primary Examiner* — Joel Lamprecht
*Assistant Examiner* — Ashish S Jasani
(74) *Attorney, Agent, or Firm* — Tucker Ellis LLP

(57) ABSTRACT

Disclosed is a method and a device for characterizing, for example identifying at least one object depicted in a raster image (1) or determining the speed of sound of the object, the raster image (1) having pixel rows and pixel columns. In order to efficiently and accurately characterize the object, the invention provides that several pixel columns (Cn) are selected and each of the selected pixel columns (Cn) is converted into a line profile (L), the amplitude of the line profile (L) representing the value (V) of image information of selected pixels of the respective selected pixel column (Cn), wherein the method comprises determining characteristics of the line profiles (L) and using the characteristics to characterize the at least one object depicted in the raster image (1).

9 Claims, 14 Drawing Sheets

(51) Int. Cl.
*G06T 7/13* (2017.01)
*G06V 10/44* (2022.01)
*G06V 10/74* (2022.01)

(52) U.S. Cl.
CPC ............ *G06V 10/44* (2022.01); *G06V 10/761* (2022.01); *G06T 2207/10132* (2013.01); *G06T 2207/30008* (2013.01)

(56) References Cited

U.S. PATENT DOCUMENTS

| 2009/0163811 | A1* | 6/2009 | Fukumoto | A61B 8/0858 |
| | | | | 600/443 |
| 2012/0116227 | A1* | 5/2012 | Suzuki | G01S 7/52073 |
| | | | | 600/443 |
| 2013/0116567 | A1* | 5/2013 | Nishigaki | G01S 15/8915 |
| | | | | 600/447 |
| 2014/0088426 | A1* | 3/2014 | Miyachi | A61B 8/5207 |
| | | | | 600/443 |

OTHER PUBLICATIONS

Shin, et al., Estimation of Average Speed of Sound Using Deconvolution of Medical Ultrasound Data, Jan. 28, 2010, 14 pages.
Wang et al Simultaneous Segmentation and Classification of Bone Surfaces from Ultrasound Using a Multi-feature Guided CNN, 2018, 9 pages.

* cited by examiner

METHOD AND DEVICE FOR CHARACTERIZING AT LEAST ONE OBJECT DEPICTED IN AN ULTRASOUND IMAGE

RELATED APPLICATION DATA

This application is a national phase application of International Application No. PCT/EP2021/068351 filed Jul. 2, 2021, which claims priority to German Application No. 10 2020 118 133.7 filed Jul. 9, 2020 and German Application No. 10 2020 118 132.9 filed Jul. 9, 2020. The contents of the aforementioned applications are incorporated herein by reference.

FIELD OF THE INVENTION

The present invention relates to a method for characterizing at least one object depicted in a raster image, the raster image being an ultrasound image, a corresponding computer program, a computer-readable storage medium storing such a program and a computer executing the program, as well as a medical system comprising an electronic data storage device and the aforementioned computer.

TECHNICAL BACKGROUND

Raster images, in particular raster images with a high noise, may be created by sweeping an area with an object of interest with an ultrasound imaging device. In order to sweep the area, for example ultrasonic, radar, sonar, X-ray, nuclear magnetic resonance, computed tomography imaging or other sweeping imaging techniques may be used. A raster image with a high noise may have a signal to noise ratio of 10:1 or less. Other values may apply for characterizing a signal to noise ratio as low, as in image processing, the height of noise in an image is often a highly subjective concept.

Methods for identifying at least one object depicted in a raster image are generally known. However, due to the high noise, borders or boundaries of the object of interest or transitions between two objects or between layers of an object cannot be identified with a high precision. Hence, with the known methods, the raster image may be insufficient in order to characterize the object. In order to characterize the object regardless of the high noise of the raster image, raw data from sweeping the area, for example with an ultrasound signal, with the object is used. However, often the raw data is not available.

Methods for determining the speed of sound are generally known. In particular when trying to measure structures of objects, for example by ultrasonic or sonar, the sound speed, in the example the speed of sound, in the object may deviate from a preset theoretical sound speed. The sound wave speed may e.g. be affected by yet unknown features like composition of the material of the object. Hence, when trying to measure structures, e.g. the size of internal structures of objects, the speed variation may lead to incorrect results. The same may be true for other methods for measuring structures of that sweep an area with an object of interest.

In view of these disadvantages, an object underlying the invention is to provide a method and an apparatus for characterizing, for example identifying at least one object depicted in a raster image or determining the speed of sound of the object with more precision and ease and without the use of raw data, i.e. based merely on the raster image.

Aspects of the present invention, examples and exemplary steps and their embodiments are disclosed in the following. Different exemplary features of the invention can be combined in accordance with the invention wherever technically expedient and feasible.

EXEMPLARY SHORT DESCRIPTION OF THE INVENTION

In the following, a short description of the specific features of the present invention is given which shall not be understood to limit the invention only to the features or a combination of the features described in this section.

The disclosed method encompasses identification of an object, for example an edge of a bone, in an ultrasound image, or determination of the speed of sound in different layers of the object by processing line profiles along a pixel column of the ultrasound image, which includes increase of the signal-to-noise ratio and subtracting an offset of selected amplitudes from the line profiles. Dynamical changes in the line profiles can then be used to estimate the thickness of the layers and subsequently determine, on the basis of knowledge about the materials of the layers, the speed of sound in the layers.

GENERAL DESCRIPTION OF THE INVENTION

The present disclosure relates to a method for identifying at least one object depicted in a raster image, the raster image having pixel rows and pixel columns.

Furthermore, the invention relates to a device for identifying at least one object depicted in a raster image, the raster image having pixel rows and pixel columns.

The object is achieved according to the invention in that several pixel columns are selected and each of the selected pixel columns is converted into a line profile, the amplitude of the line profile representing the value of image information of selected pixels of the respective selected pixel column, wherein the method comprises determining characteristics of the line profiles and using the characteristics to characterize the at least one object depicted in the image.

Furthermore, the object is achieved according to the invention in that the method comprises the steps of selecting a B-mode image of a cross section of the multilayer object, the B-mode image being created by introducing the sound into the object, receiving a reflected sound, the reflected sound being formed by reflecting the introduced sound at the boundaries of the layers, and creating the B-mode image of the cross section of the layers based on the reflected sound, the B-mode image being a raster image, the raster image having pixel rows and pixel columns. Further, the method comprises the steps of estimating the layers and their material based on their sequence in the B-mode image, wherein several pixel columns are selected and each of the selected pixel columns is converted into a line profile, the amplitude of the line profile representing the value of image information of selected pixels of the respective selected pixel column, wherein the method comprises determining characteristics of the line profiles and using the characteristics determine the speed of the sound in at least one of the layers.

For the above-mentioned device, the object is achieved according to the invention in that the device is adapted to perform the method according to the invention.

Hence, the sound speed can be determined after the measurement is done and based on the B-mode image, which is readily accessible. With the detected sound speed, locations of objects or their borders can be determined more precisely than with a default sound speed.

For the above-mentioned device, the object is achieved according to the invention in that the device is adapted to perform the method according to the invention.

As the method uses the raster image instead of the raw data (in particular in case ultrasound is used), it is not necessary anymore to create access to the raw data. Instead, the readily available raster image can be used. By selecting a pixel column and creating the line profile, the characteristics can be determined with a low amount of data and a reduced set of calculations, which reduces the time required for the characterization. Optionally, a plurality or all of the pixel columns may be selected. The solution according to the invention can be further improved by the following example that are advantageous on their own, in each case, and can be combined as desired.

According to an example, the method comprises processing the selected line profiles to form a processed line profile from each of the selected line profiles, the processed line profiles having an enhanced signal to noise ratio compared to the respective selected line profile.

Processing the selected line profiles to form a processed line profile may comprise determining derivates, curvatures, amplitudes and/or amplitude changes of the selected line profiles. Alternatively or additionally, processing the selected line profiles to form a processed line profile may comprise filtering the selected line profiles.

Possible processing steps and/or exemplary calculations may be disclosed in "Proceedings of the 29th Annual International Conference of the IEEE EMBS; Cité Internationale, Lyon, France, Aug. 23-26, 2007 —An algorithm for QRS onset and offset detection in single lead electrocardiogram records", whose content is incorporated by reference, for example concerning the possible processing steps and/or exemplary calculations. An advantage of this example may be that the characteristics of the object are more distinct in the processed line profile than in the respective selected line profile.

According to an example, processing the selected line profiles to form a processed line profile comprises determining individual offset values for selected amplitudes of selected line profiles and subtracting the individual offset values from the respective amplitude prior to determining the characteristics of the line profiles to create the processed line profile. A further advantage of this example may be that even noisy images like B-mode images, which may have a signal to noise ratio of 10:1 or less, can be used to determine the sound speed.

For estimating a baseline, a filter may be used. A filter may be a mathematical construct. An example of a filter is disclosed in "IEEEAccess, 2019, Volume 7, 159754-159772—Cardiotocographic Signal Feature Extraction Through CEEMDAN and Time-Varying Autoregressive Spectral-Based Analysis for Fetal Welfare Assessment", whose content, in particular of section B2, is incorporated by reference. An advantage of this example may be that the characteristics of the object are more distinct in the processed line profile than in the respective selected line profile.

According to an example, the characteristic of the line profiles are zero crossings of the processed line profiles. An advantage of this example may be that zero crossings are generally very precise and may allow for a precise characterization of the object.

According to an example, the method comprises determining different aspects of the processed line profile by performing signal decomposition of the processed line profile. For example, the method comprises decomposing the processed line profile into n-empirical modes, wherein n is 1, 2, 3, 4 or 5 to form a decomposed line profile.

The signal decomposition may comprise applying a filter bank, complex wavelet transformation, discrete wavelet transformation, empirical mode decomposition (Hilbert-Huang transformation). A filter bank may be a set of digital filters that are applied to an input signal. Each digital filter may have a different central frequency and may have the same bandwidth. An example of empirical mode decomposition is provided in EEEAccess, 2019, Volume 7, 159754-159772—Cardiotocographic Signal Feature Extraction Through CEEMDAN and Time-Varying Autoregressive Spectral-Based Analysis for Fetal Welfare Assessment, in particular in section B5 thereof, whose content is incorporated by reference. In this case, a cardiotocographic signal is analyzed, but it would be the same procedure with the preprocessed line profile.

An advantage of this example may be that the characteristics of the object are even more distinct in a decomposed signal than in the respective selected line profile or the processed line profile, the decomposed signal being formed by performing signal decomposition of the processed line profile. A further advantage of this example may be that the sound speed can be determined more easily and/or with higher accuracy from a decomposed signal, the decomposed signal being formed by performing signal decomposition of the processed line profile.

According to an example, the method comprises determining different frequency changes in time as a result from the changes in structure at boundaries between the layers from the decomposed line profile by pole-tracking. Time-variant auto-regressive modeling to extract time-variant poles may be used.

According to an example, the method comprises determining dynamics of the processed line profile or of the decomposed signal.

Determining dynamics of the processed line profile may be done by modelling the time variance or pole tracking.

Pole tracking is described e.g. in SCIENTIFIC REPORTS | (2018) 8:12070—Novel clinical device tracking and tissue event characterization using proximally placed audio signal acquisition and processing, in particular in the section "Time-varying auto-regressive modelling for acoustic signature extraction.", whose content is incorporated by reference.

An advantage of this example may be that possible or expected characteristics of the object can be used when modelling, such that a good model may directly lead to the real characteristics of the object.

According to an example, the method comprises deriving space variant information from the determined dynamics of the processed line profile.

The space variant information may be derived from the modelled time variance. Once that the poles are computed, there can be several ways to acquire information from them. One possibility is to track the maximal energy pole as explained e.g. in SCIENTIFIC REPORTS |(2018) 8:12070—Novel clinical device tracking and tissue event characterization using proximally placed audio signal acquisition and processing, whose content is incorporated by reference. An advantage of this example may be that the sound speed can be determined more easily and/or with higher accuracy.

According to an example, the method comprises extracting the layer thickness from the detected dynamical changes of the line profile as presented further below before the description of the exemplary examples. An advantage of this example may be that the sound speed can be determined more easily or with higher accuracy. Additionally, the workflow previously used for taking a B-mode image and for identifying the location of an object or its border our boundary can be maintained.

An advantage of this example may be that the real characteristics of the object can be allotted spatially, such that not only the characteristics of the object, but also the size of the object and even of layers with different characteristics of the object can be determined.

According to an example, the method comprises detecting dynamical changes in the processed line profile, in the decomposed signal, in the time variant information and/or in the space variant information.

Detecting dynamical changes may be performed by applying cumulative sum control chart or statistical hypothesis testing to the determined dynamics. An exemplary way for this is disclosed e.g. in "Proceedings of the 29th Annual International Conference of the IEEE EMBS; Cité Internationale, Lyon, France, Aug. 23-26, 2007—An algorithm for QRS onset and offset detection in single lead electrocardiogram records", in particular in section IIID thereof, whose content is incorporated by reference.

An advantage of this example may be that the detected dynamical changes may even more precisely represent the characteristics of the object.

According to an example, the method comprises providing pre-known candidates for the at least one object or its layers and comparing dynamical change data of the pre-known candidates with the detected dynamical changes. An advantage of this example may be that using pre-known candidates allows for an easy determination of the characteristics of the object while reducing the risk of fundamentally false determinations of the characteristics.

According to an example, the method comprises performing selected steps of the above steps for selected of the line profiles and determine the consistency of the detected dynamical changes over the selected line profiles. An advantage of this example may be that spatial continuity between selected of the line profiles and in particular between adjacent line profiles improves confidence in the determined characteristics.

According to an example, the method comprises applying an artificial intelligence for comparing the dynamical change data with the detected dynamical changes. An advantage of this example may be that applying an artificial intelligence quickly improves confidence in the determined characteristics.

According to an example, the method comprises applying an artificial intelligence for determining the consistency of the detected dynamical changes over the selected line profiles.

An advantage of this example may be that applying an artificial intelligence quickly improves confidence in the determined characteristics.

According to an example, the method comprises setting a boundary of the at least one object as the identifying feature of the at least one object based on detected dynamical changes with a consistency higher than a pre-defined value.

An advantage of this example may be that objects, areas of layers of objects with different characteristics can be distinguished from each other with a pre-defined confidence.

According to an example, the method comprises identifying boundaries of several different objects depicted in the raster image. An advantage of this example may be that the structure of a body, for example the internal structure of a human body depicted in the raster image, can be determined swiftly and with high accuracy.

According to an example, the raster image is a B-mode ultrasound image.

According to an example, the device is an ultrasonic, radar, sonar, X-ray, nuclear magnetic resonance, computed tomography imaging device with an ultrasonic, radar, sonar, X-ray, nuclear magnetic resonance, computed tomography detector. An advantage of this example may be that the raster image of the object can easily be created and the object can almost instantly be characterized.

The term "selected" can mean that single, less than all or all items the word "selected" refers to are selected. The object may comprise layers or may be a layer of a multilayer object.

The invention is disclosed further below from another perspective in connection with the figures, an in particular the layer thickness may be extracted from the detected dynamical changes of the line profile as exemplarily described further below with reference to the figures.

In this section, a description of the general features of the present invention is given.

In general, the invention reaches the aforementioned object by providing, in a first aspect, a method for characterizing at least one object depicted in a raster image, the raster image being an ultrasound image having pixel rows and pixel columns. For example, the raster image is a B-mode ultrasound image. The image can be two-dimensional or three-dimensional (i.e. a tomographic image). The object is for example a multilayer object and for example bony tissue or cartilage, an organ, a vessel, a tissue boundary, an implant or a medical instrument. The term "pixel" therefore encompasses both pixels as usually understood and voxels. For example, the method is a computer-implemented medical method. The method comprises for example executing, on at least one processor of at least one computer (for example at least one computer being part of a navigation system), the following exemplary steps which are executed by the at least one processor. However, execution of the method by a computer is not mandatory.

In a (for example first) exemplary step, at least one pixel column is selected and the selected pixel column is converted into a line profile, the amplitude of the line profile representing the value of image information of selected pixels of the selected pixel column.

In a (for example second) exemplary step, characteristics of the line profile are determined and the characteristics are used to characterize the at least one object depicted in the raster image. The profile runs from a position closest to the position of an ultrasound imaging device used to generate the raster image to a position farther away from the position of the ultrasound imaging device. For example, the profile runs from a skin surface of an anatomical body part to bony tissues included in the anatomical body part. The characteristics of the selected line profile are for example values of the selected profile indicating the position of an edge of the object, for example values of the selected profile being associated, among the values of the selected profiles, with a greatest distance from a predetermined position, for example a position of an ultrasound imaging device used to generate the raster image, and having a predetermined relationship to a threshold value such as zero crossings of the processed line profile.

In a (for example third) exemplary step, the selected line profile is processed to form a processed line profile, the processed line profile having an enhanced signal to noise ratio compared to the respective selected line profile. processing the selected line profile to form a processed line profile comprises determining individual offset values for selected amplitudes of the selected line profile and subtracting the individual offset values from the respective amplitude prior to determining the characteristics of the line profile to create the processed line profile. Thereby, the position of for example an edge of the object in the image can be determined and/or corrected. For example, the position of an edge of a bone can be determined and/or corrected in order to register a patient with a reference system used to conduct a navigated medical procedure, i.e. to transform the patient's position into that reference system. For example, the ultrasound imaging device used to generate the raster image is navigated and the raster image and/or the anatomical body part can thereby be registered with a two- or three-dimensional planning image data set used for planning the medical procedure. In an example, processing the selected line profile to form processed line profile comprises calculating the curvature of the selected line profile.

In an example of the method according to the first aspect, several pixel columns are selected and each of the selected pixel columns is converted into a line profile and the characteristics are determined of each of the line profiles and each of the line profiles is processed to form a processed line profile. The method the comprises for example the following steps:
  detecting dynamical changes in the processed line profile; and
  setting a boundary of the at least one object as the identifying feature of the at least one object based on detected dynamical changes.

In a development of this example, the object is a multi-layer object and the object comprises layers of known materials and sequence but with unknown layer thicknesses. The method then comprises for example steps of
  estimating the layers and their material based on their sequence in the raster image; and
  using the determined characteristics of the line profiles to determine the speed of sound in at least one of the layers.

Additionally to this development of this example, the method comprises for example
  selecting a raster image of a cross section of the multilayer object, the raster image being created by
    introducing the sound into the object,
    receiving a reflected sound, the reflected sound being formed by
    reflecting the introduced sound at the boundaries of the layers, and
    creating the raster image of the cross section of the layers based on the reflected sound.

In an example, the method according to the first aspect comprises determining different aspects of the processed line profile by performing signal decomposition (for example, by Fourier or wavelet transformation of empirical mode decomposition) of the processed line profile.

In an example, the method according to the first aspect comprises determining dynamics of the processed line profile.

In an example, the method according to the first aspect comprises deriving space variant information from the determined dynamics of the processed line profile (P, E).

In an example, the method according to the first aspect comprises providing pre-known candidates for the at least one object and comparing dynamical change data of the pre-known candidates with the detected dynamical changes.

In an example, the method according to the first aspect comprises performing selected steps of the steps of any one of the preceding claims for the line profiles and determine the consistency of the detected dynamical changes over the selected line profile. In this example, the method comprises for example applying an artificial intelligence for comparing the dynamical change data with the detected dynamical changes and/or applying an artificial intelligence for determining the consistency of the detected dynamical changes over the selected line profile. In a further development of this example of the method according the first aspect comprises the setting the boundary of the at least one object as the identifying feature of the at least one object is performed based on detected dynamical changes with a consistency higher than a pre-defined value. In a further development of this example of the method according the first aspect comprises identifying boundaries of several different objects depicted in the raster image.

In an example of the method according to the first aspect, a correction factor per line profile is estimated that is used to rectify the position of the object and reconstruct a final image in which the estimated rectified version of the object is displayed.

In an example, the method according to the first aspect comprises decomposing the processed line profile into n-empirical modes, wherein n is 1, 2, 3, 4 or 5 to form a decomposed line profile. As an optional development of this example, the method comprises determining different (i.e. multiple) frequency changes in time as a result from the changes in structure at the boundaries from the decomposed line profile by pole-tracking.

In a second aspect, the invention is directed to a computer program comprising instructions which, when the program is executed by at least one computer, causes the at least one computer to carry out method according to the first aspect. The invention may alternatively or additionally relate to a (physical, for example electrical, for example technically generated) signal wave, for example a digital signal wave, such as an electromagnetic carrier wave carrying information which represents the program, for example the aforementioned program, which for example comprises code means which are adapted to perform any or all of the steps of the method according to the first aspect. The signal wave is in one example a data carrier signal carrying the aforementioned computer program. A computer program stored on a disc is a data file, and when the file is read out and transmitted it becomes a data stream for example in the form of a (physical, for example electrical, for example technically generated) signal. The signal can be implemented as the signal wave, for example as the electromagnetic carrier wave which is described herein. For example, the signal, for example the signal wave is constituted to be transmitted via a computer network, for example LAN, WLAN, WAN, mobile network, for example the internet. For example, the signal, for example the signal wave, is constituted to be transmitted by optic or acoustic data transmission. The invention according to the second aspect therefore may alternatively or additionally relate to a data stream representative of the aforementioned program, i.e. comprising the program.

In a third aspect, the invention is directed to a computer-readable storage medium on which the program according to the second aspect is stored. The program storage medium is for example non-transitory.

In a fourth aspect, the invention is directed to at least one computer (for example, a computer), comprising at least one processor (for example, a processor), wherein the program according to the second aspect is executed by the processor, or wherein the at least one computer comprises the computer-readable storage medium according to the third aspect.

In a fifth aspect, the invention is directed to a medical system, comprising:
a) the at least one computer according to the fourth aspect; and
b) a medical ultrasound imaging device for carrying out ultrasound imaging on the patient,
wherein the at least one computer is operably coupled to the ultrasound imaging device for receiving a signal from the medical device corresponding to the raster image for processing the raster image by executing the program.

The present invention also relates to the use of the device/system or any embodiment thereof for processing a raster image being an ultrasound image, wherein the use comprises execution of the steps of the method according to the first aspect.

In a sixth aspect, the present invention relates to a device for characterizing at least one object depicted in a raster image, for example identifying the object or determining the speed of sound of the object, the raster image having pixel rows and pixel columns, wherein the device is adapted to perform the method according to the first aspect.

Definitions

In this section, definitions for specific terminology used in this disclosure are offered which also form part of the present disclosure.

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating or determining steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term computer includes a server resource. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is a virtual reality device or an augmented reality device (also referred to as virtual reality glasses or augmented reality glasses) which can be used as "goggles" for navigating. A specific example of such augmented reality glasses is Google Glass (a trademark of Google, Inc.). An augmented reality device or a virtual reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. An example of such a digital lightbox is Buzz®, a product of Brainlab AG. The monitor may also be the monitor of a portable, for example handheld, device such as a smart phone or personal digital assistant or digital media player.

The invention also relates to a computer program comprising instructions which, when on the program is executed by a computer, cause the computer to carry out the method or methods, for example, the steps of the method or methods, described herein and/or to a computer-readable storage medium (for example, a non-transitory computer-readable storage medium) on which the program is stored and/or to a computer comprising said program storage medium and/or to a (physical, for example electrical, for example technically generated) signal wave, for example a digital signal wave, such as an electromagnetic carrier wave carrying information which represents the program, for example the aforementioned program, which for example comprises code means which are adapted to perform any or all of the method steps described herein. The signal wave is in one example a data carrier signal carrying the aforementioned computer program. The invention also relates to a computer comprising at least one processor and/or the aforementioned computer-readable data storage medium and for example a memory, wherein the program is executed by the processor.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing (and e.g. outputting) the data by means of a computer and for example within the framework of the method in accordance with the invention. A step of "determining" as described herein for example comprises or consists of issuing a command to perform the determination described herein. For example, the step comprises or consists of issuing a command to cause a computer, for example a remote computer, for example a remote server, for example in the cloud, to perform the determination. Alternatively or additionally, a step of "determination" as described herein for example comprises or consists of receiving the data resulting from the determination described herein, for example receiving the resulting data from the remote computer, for example from that remote computer which has been caused to perform the determination. The meaning of "acquiring data" also for example encompasses the scenario in which the data are received or retrieved by (e.g. input to) the computer implemented method or program, for example from another program, a previous method step or a data storage medium, for example for further processing by the computer implemented method or program. Generation of the data to be acquired may but need not be part of the method in accordance with the invention. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

BRIEF DESCRIPTION OF THE DRAWINGS

In the following, the invention is described with reference to the appended figures which give background explanations and represent specific embodiments of the invention. The scope of the invention is however not limited to the specific features disclosed in the context of the figures, wherein.

DESCRIPTION OF EMBODIMENTS

Figure 1:
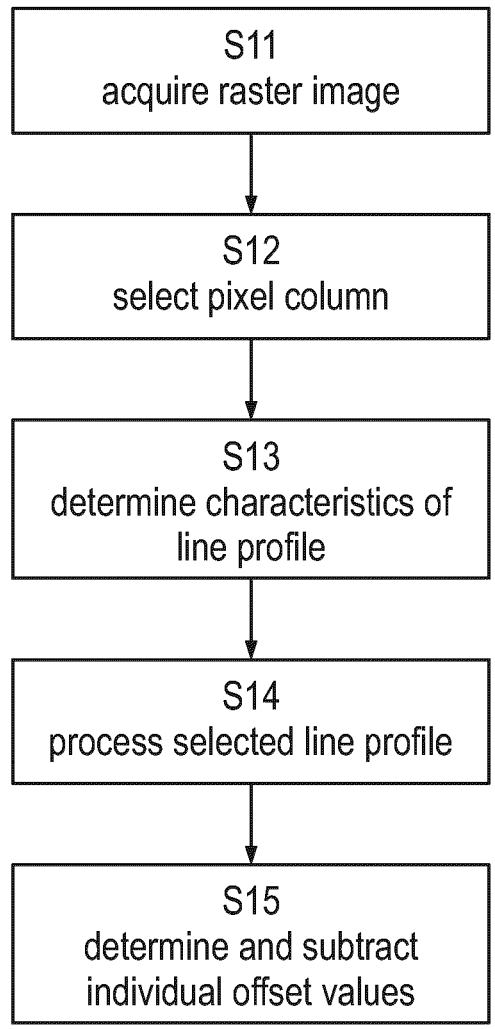
FIG. 1 illustrates the basic steps of the method according to the first aspect.

FIG. 1 illustrates the basic steps of the method according to the first aspect, in which step S11 encompasses acquisition of the raster image, step S12 encompasses selection of the pixel column and subsequent step S13 encompasses determining characteristics of the line profile. In step S14, the selected line profile is processed, which includes determining and subtracting the individual offset values in step S15.

Ultrasound (US) imaging is increasingly used in navigated surgery. US is a cheap, portable and versatile imaging modality that has made considerable progress in imaging quality and usage in many interventional surgeries. These advantages make that US can become the ideal replacement of computed tomography in lumbar spinal surgeries. However, spatial information quality in US is relatively inferior to other image modalities. One of the main limitations in US-guided procedures is the speed of sound variation throughout the different tissues of the body. These speed of sound variations can provoke high variability of bones appearance and shape resulting in location errors that can have a significant effect in spinal surgery.

In traditional delay-and-sum beam-forming design, a constant speed of sound of 1540 m/s is generally used. The assumption of a constant speed of sound in different layers of soft tissues leads to lateral de-focusing and blurring, loss of image contrast due to increased acoustic clutter, and calculation inaccuracies. All this potentially leads to errors in localizing tissues in B-mode images. Each soft tissue has a different average speed of sound, as presented in different publications [1-3]. The discrepancy between the fixed speed of sound value of 1540 m/s in human soft tissues and its actual inhomogeneous distribution leads to small but systematic errors of up to a few millimeters. These errors occur in the line of direction of scanned structures and may degrade the accuracy of clinical diagnoses and intra-operative US imaging.

In this disclosure, a new methodology for speed of sound calibration for rectifying the localization of bones in US images using a deep learning-based bone segmentation method and an innovative approach for identifying boundaries (between two tissues, for example) in highly noisy images is presented. We have additionally evaluated the effects of speed of sound in a phantom involving ex-vivo tissues and also in real subjects by modifying the average speed of sound of a US device.

Figure 2:
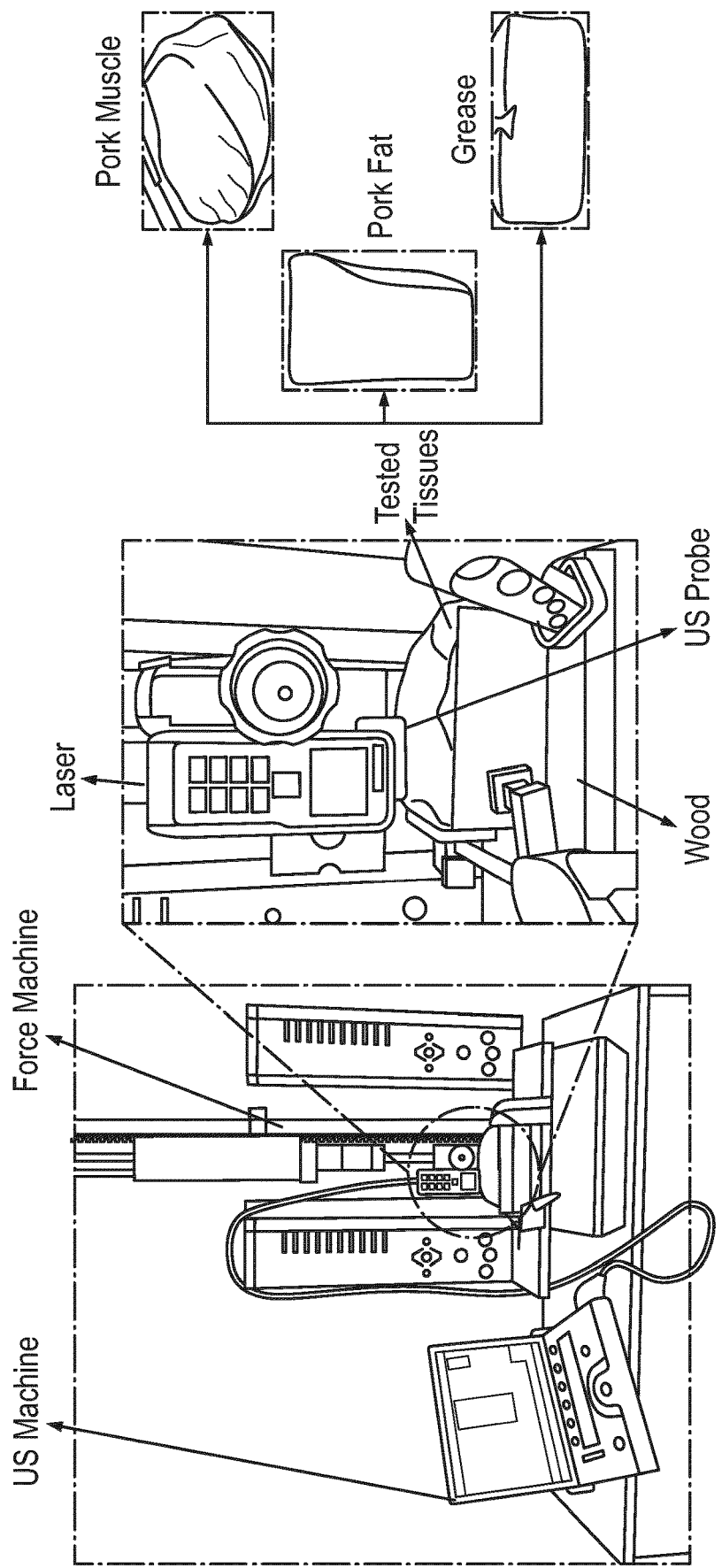
FIG. 2 shows an embodiment of the present invention, specifically the method according to the first aspect.

For evaluating the effects of speed of sound, a first experimental setup was designed (see FIG. 2). A phantom consisting of a layer of a specific ex-vivo tissue over a piece of wood (emulating bone [4]) was imaged using a GE Logiq E US device and a 9 L linear probe. A testing machine (Zwicki, Zwick GmbH & Co. KG, Ulm) was used in order to measure automatically and accurately the distance between the US probe and the border of the wood. Three types of ex-vivo pork tissues at different thicknesses were tested: muscle, fat, and grease.

Speed of sound effects are evaluated mainly through the error computation between the real and estimated measurements of the distance between the US probe and the surface of the wood sample. The real distance is provided by the testing machine, and the estimated distance is extracted from the US image. The extraction of the estimated distance was performed using two methods. The first method comprises using only the central line profile for the location of the wood sample surface while the second approach comprises extracting the line profiles of selected columns or of every column of the US image matrix and then to average them in order to find the location of the wood surface. This second approach may avoid problems of location when the wood boundary does not appear clearly in the central line profile of the US image.

Figure 3:
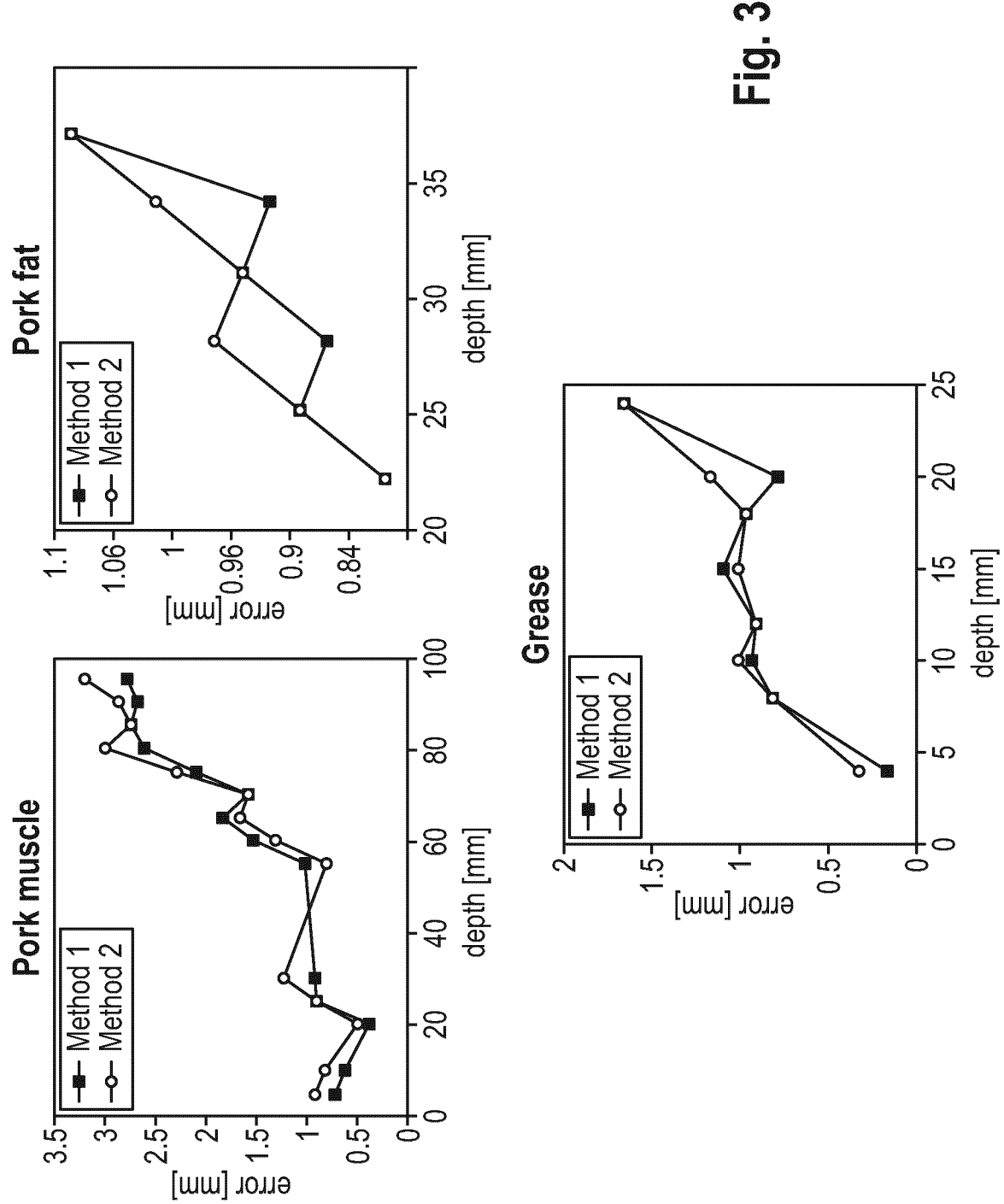
FIG. 3 shows errors between real and estimated distance to the wood measurements for three tissues: pork muscle, pork fat and grease.

FIG. 3 exemplarily shows the errors between real and estimated US measurements for the three tested tissues. It is possible to observe (for both methods of distance estimation) that for all the tested tissues, the error increases when the tissue thickness increases. In the exemplary case of pork muscle, the error varies from 0.5 mm to 3.2 mm when the muscle thickness increases from 5 to 95 mm. For pork fat, errors go from 0.82 mm to 1.1 mm when the fat thickness varies from 22 to 37 mm and for grease errors vary from 0.3 mm to 1.7 mm when grease thickness varies from 4 to 24 mm.

Figure 4:
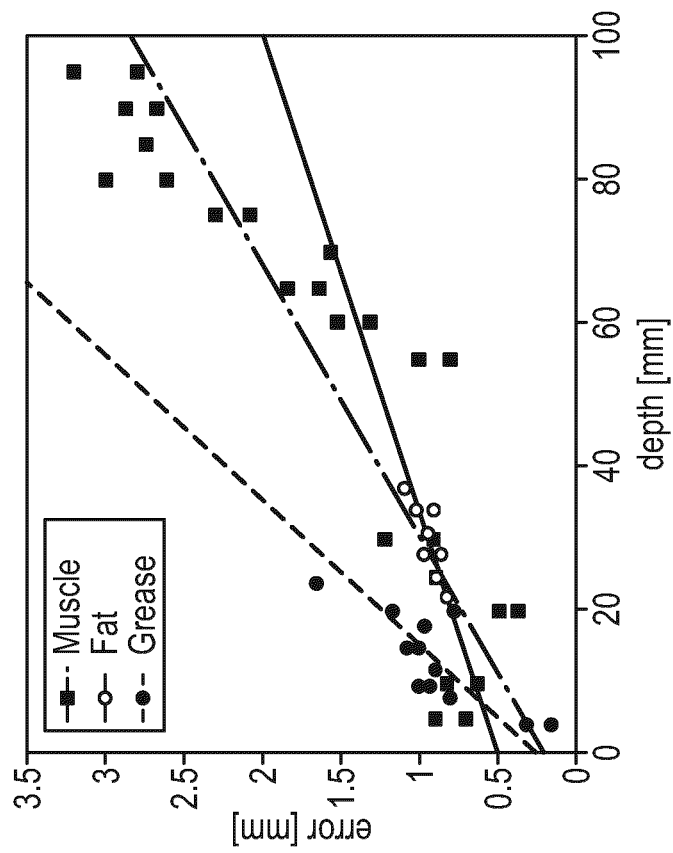
FIG. 4 illustrates a comparison of errors between the three tested tissues and linear regression of the obtained errors.
Figure 4:
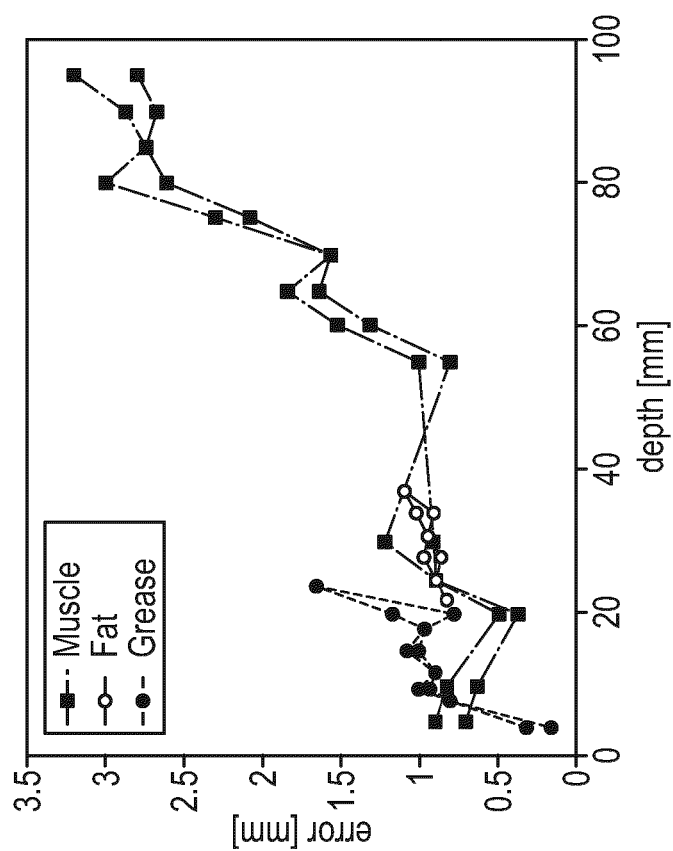

FIG. 4 shows a comparison of the error variation between the three tested tissues. A linear regression of these errors allows us to observe that the influence in the speed of sound errors are different depending on the tissue tested. The slope of the errors seems to be more significant for grease than for muscle or fat.

Figure 5:
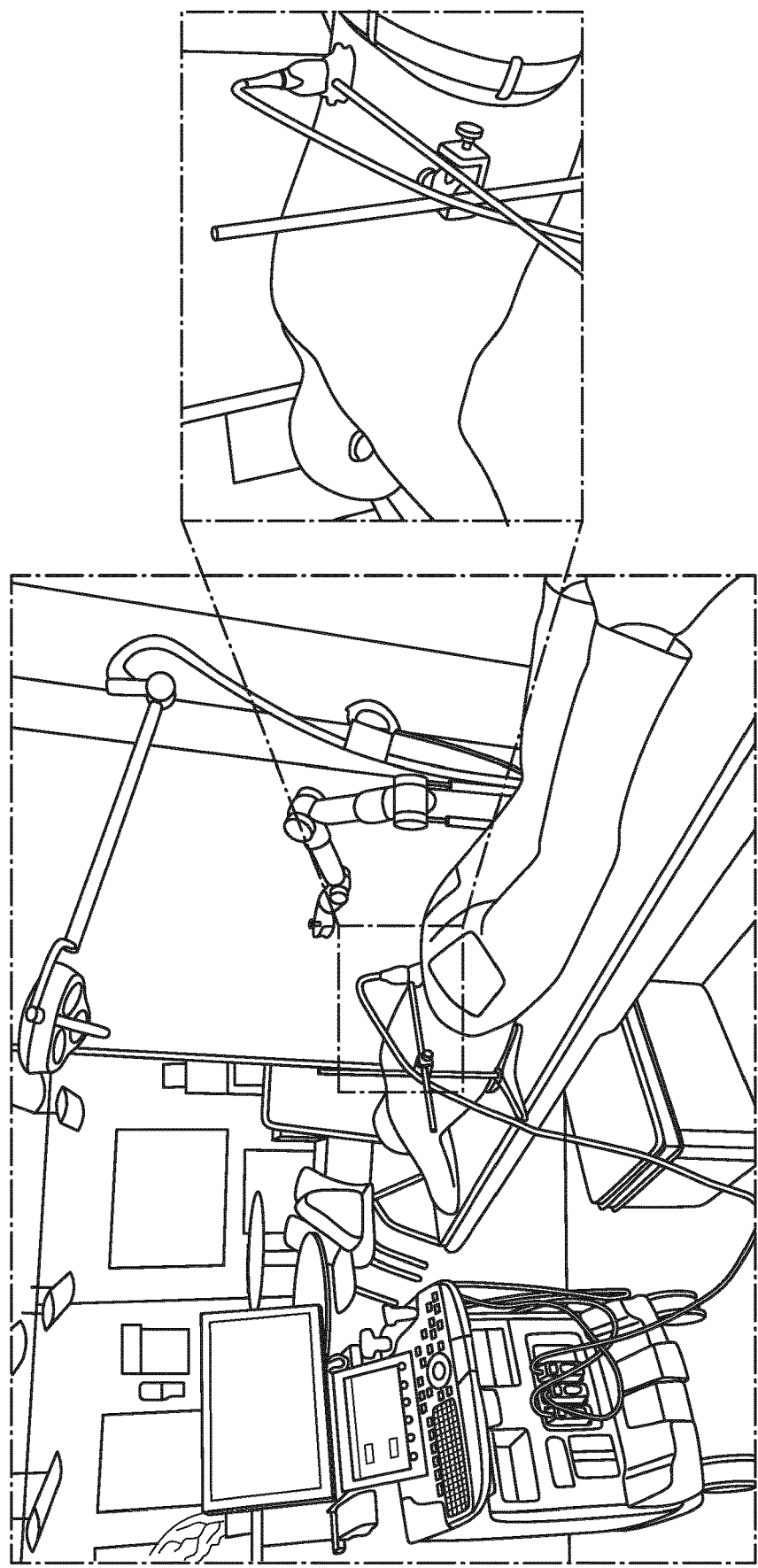
FIG. 5 shows an ultrasound image acquisition setup in a real subject with different fixed speeds of sound.

In order to confirm these results, a second experiment has been performed in real subjects. US images were acquired from real subjects with a Logic E10 US device using a 7 MHz L2-9 probe. This US device allows the modification of the fixed speed of sound. The spine of the subject was imaged using seven different speed of sound, from 1400 m/s to 1620 m/s, increasing in steps of 20 m/s. The probe was fixed to the surface of the body, and the US image was acquired during a short apnea episode of the tested subject (see FIG. 5).

Figure 6:
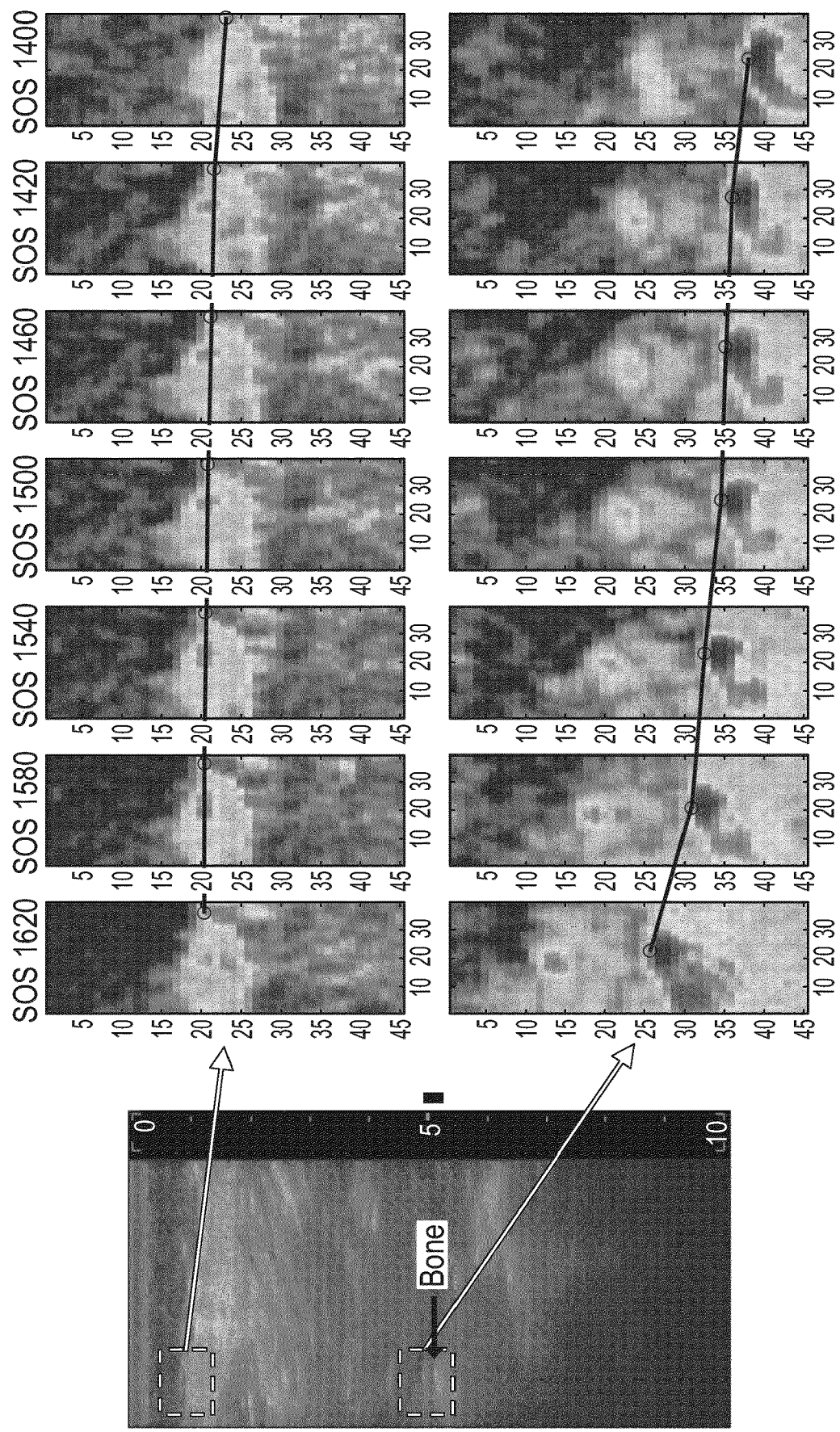
FIG. 6 shows a comparison of localization of a fiducial point between a layer near the body surface and the bone layer for different speeds of sound.

FIG. 6 shows how fiducial points in a superficial layer and at bone location (5 cm depth) shift when the Speed of sound is modified. The error between the bone location with Speed of sound 1620 m/s and Speed of sound 1400 m/s is around 1.74 mm. It is possible to verify that the difference of location for the surface fiducial point is minimal compared to the fiducial point located on the bone surface.

Figure 7:
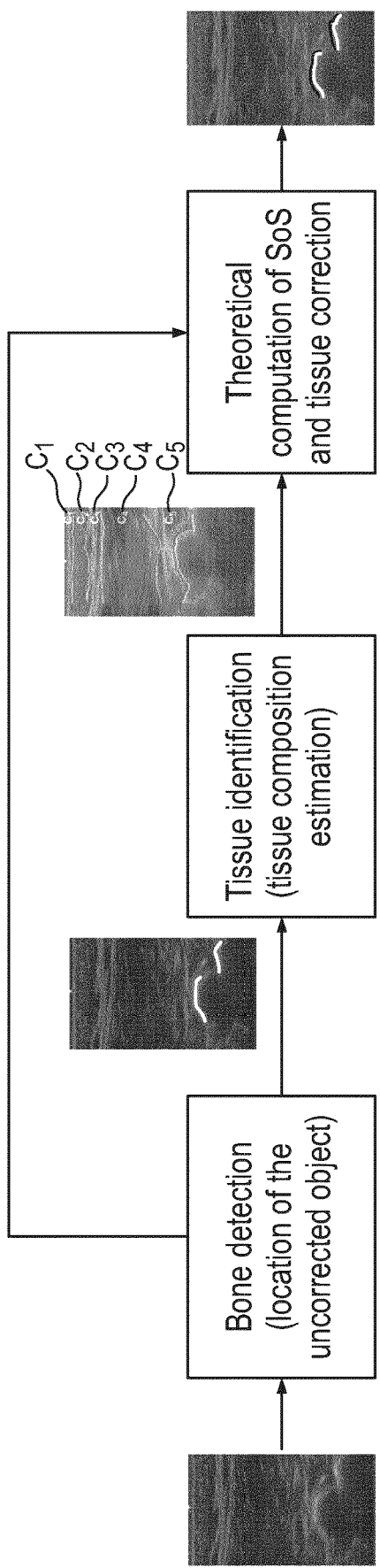
FIG. 7 is a general block diagram of the disclosed approach for speed of sound calibration for bone.

Disclosed is a novel strategy for speed of sound calibration for bone rectification in US images. The strategy involves three steps (see the diagram of FIG. 7): bone detection using a Deep Learning approach, tissue identification, and theoretical computation of the speed of sound.

First of all, it is required to perform detection of the bone in the US image. This step will provide a first uncorrected location estimation of the bone. The second step comprises identifying in the US image every tissue preceding bone in order to know how the speed of sound will vary before its arrival to the bone. Finally, using a theoretical background of the behavior of the speed of sound in different tissues, it is possible to estimate a rectification factor for every pixel belonging to bone. In order to detect bone structures in US images, a direct image-based segmentation method is performed. For that, a Convolutional Neural Network (CNN) based on a U-Net architecture is used for having a first prediction of the bone location.

Figure 8:
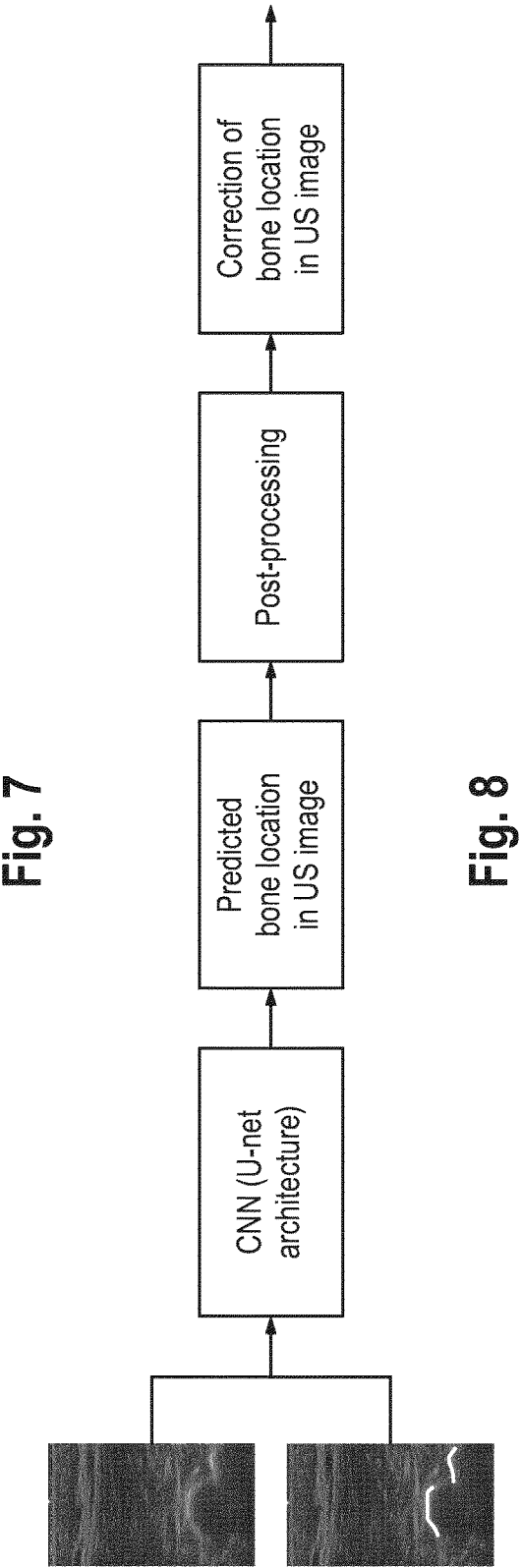
FIG. 8 illustrates steps for bone segmentation in ultrasound images.
Figure 9:
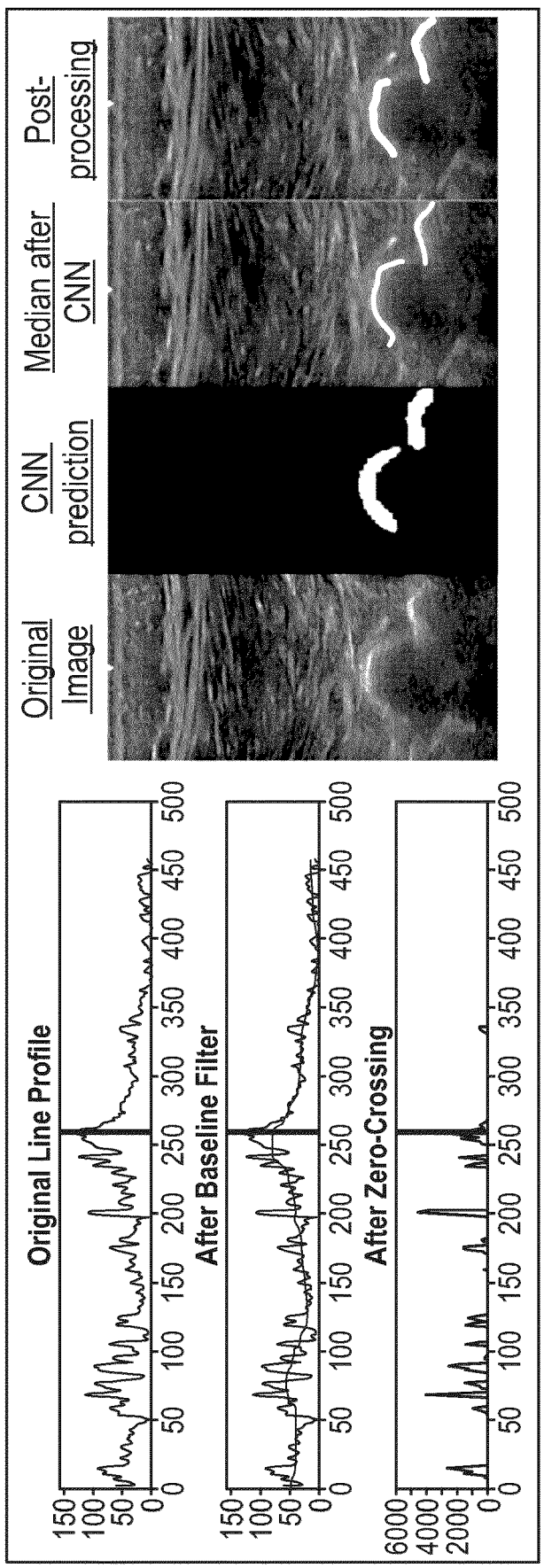
FIG. 9 illustrates the post-processing of the automatically segmented ultrasound image.

CNN has been already used for US bone segmentation [5-7]. However, the predicted pixels as bones sometimes are not exactly located on the bone surface, which can be a problem in case of high precision requirements. The main novelty of the proposed method for bone detection is that after a first prediction of the bone, a post-processing step is used in order to find the exact location of the bone surface in the US image. The diagram of FIG. 8 shows the main steps of the approach. The CNN is first trained using the original US image and a set of manually segmented (ground truth) images in order to estimate a model for obtaining a first prediction of the bone location. The post-processing step applied later consists of a correction per column line profile. For that, each column line profile signal where bone was predicted is first detrended and then zero-crossed. Finally, a normalized cross-correlation is applied to the resulting signal in order to capture the shadowing effects and then to correct the pixel position of the bone to the sample when this effect starts (see FIG. 9). FIG. 9 shows that a line profile is supplemented by a running average of the line profile and that all values below the baseline of the running average are cut off. The edge of a bone facing the ultrasound imaging device is the remaining peak lying above a predetermined threshold and associated with a position farthest away from the position of the ultrasound imaging device.

Figure 10:
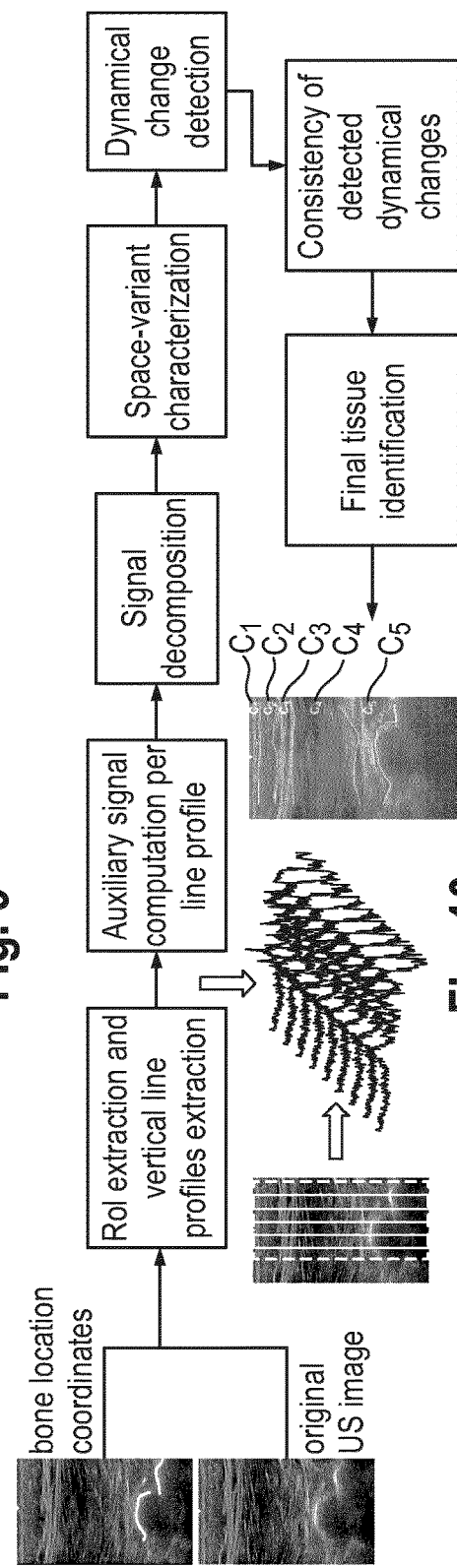
FIG. 10 shows a tissue identification general block diagram.

A step for performing speed of sound calibration in order to correct the bone position is to identify each tissue that precedes the bone to be able to compute a tissue-dependent speed of sound. This task is highly challenging due to the low SNR of the US image that makes that boundaries between different tissues are drawn in noise, making difficult their identification even with naked eyes. Additionally, the connective tissue and the non-homogeneity nature of a given tissue, which can even be composed of different sub-tissues, make the problem even more challenging. For that reason, the solution of the problem can not be addressed as a standard image processing segmentation problem but as a dynamical change problem where space-variant echogenicity characteristic changes have to be detected. Each dynamical change should correspond to borders between tissues. We propose a new approach that takes the boundary detection problem as a space-variant dynamical change problem, where each line profile of the image is taken as a signal where dynamical changes occur and need to be detected. The detected changes correspond to boundaries between tissues. The main idea of the approach is to take one each vertical line profile or a plurality of line profiles of an image and to search for abrupt dynamical changes using a parametrical model of the line profile that allows for tracking such dynamics in the signal. For that, we propose a signal processing strategy that receives as input the preliminary bone location coordinates (computed with the method presented in Section 3.1) and the original US image. The strategy involves seven main steps, as shown in FIG. 10:

RoI (region of interest) and vertical line profiles extraction: in this step, we first identify a sub-image RoI involving regions of the image where the bone is located. Then, each column line profile signal is extracted from the RoI.

Auxiliary signal computation: the main objective of this step is to compute an indicator or auxiliary signal per line profile that intends to enhance significant dynamical changes in the line profile signal. Indicators can be based on different types of features such as curvature, derivative, amplitude, variance, higher-order statistics, among others. The auxiliary signal can also be a function (linear or non-linear) of different feature indicators.

Signal decomposition: in order to separate the main aspects/dynamics that a line profile signal involves, the auxiliary signal of each line profile is decomposed in different frequencies/scales/modes. For that, different decomposition methods can be used, such as Filter banks, adaptive filtering, Continuous Wavelet Transformation, Discrete Wavelet Transformation, Empirical Mode Decomposition (EMD), among others.

Space-variant characterization: in this step, the resulting auxiliary signal is characterized using a parametrical representation or model. The main objective of this model is to extract parametrical features that serve to track and enhance the dynamical changes that occur in the auxiliary signal. A time-variant autoregressive (TV-AR) parametrical model can be used to track the signal dynamics through a parametrized time-variant spectrum or pole-based tracking techniques [8, 9].

Dynamical change detection: a change detection algorithm is necessary in order to detect the pixel samples where dynamical changes occur. Different types of algorithms can be used here, going from simple thresholding or decision rules to more advanced algorithms as hypothesis testing or CUSUM test. The detected pixel samples should correspond to tissue echogenicity changes produced by a layer-to-layer boundary.

Consistency of detected dynamical changes: the goal of this step is to identify false positives and correction of detected dynamical changes. For that, a consistency analysis is performed over the different changes detected in the whole set of line profiles signals belonging to the RoI.

Final tissue identification: using information about samples where tissue changes occur, their texture, and the anatomical order of layers, it is possible to parametrize every tissue structure preceding bone.

Figure 11:
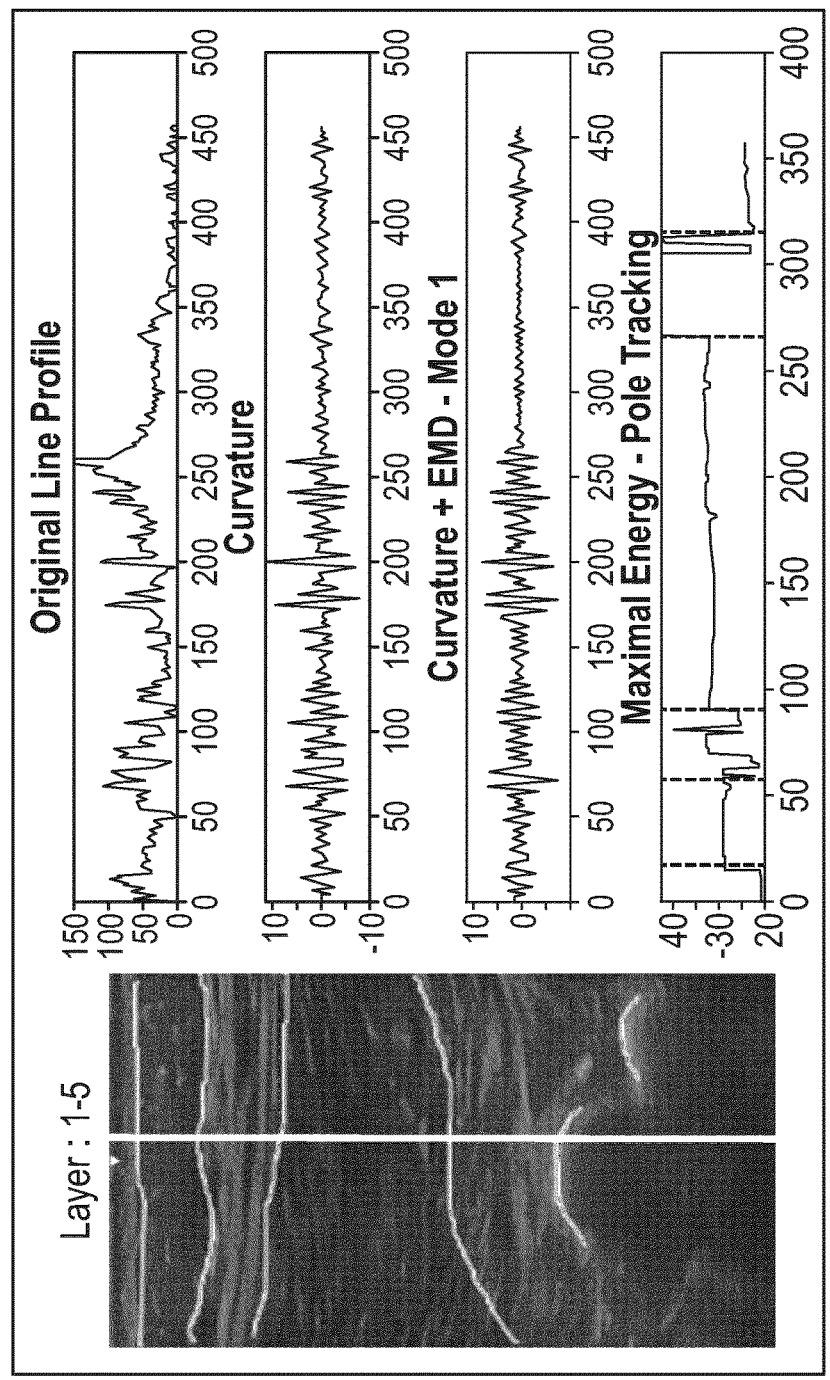
FIG. 11 is example of tracking dynamical changes in a line profile extracted from an ultrasound signal.
Figure 11:
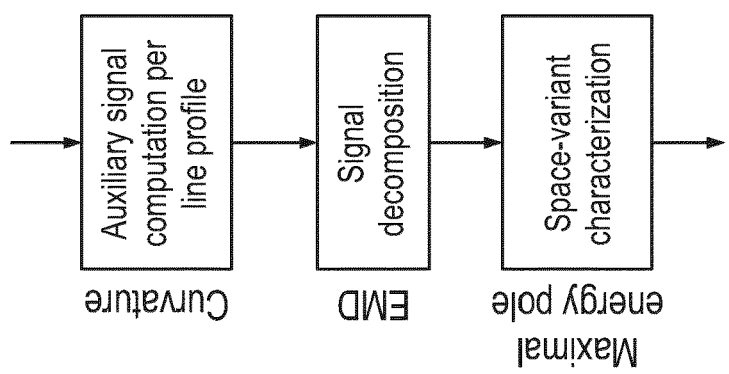
Figure 12:
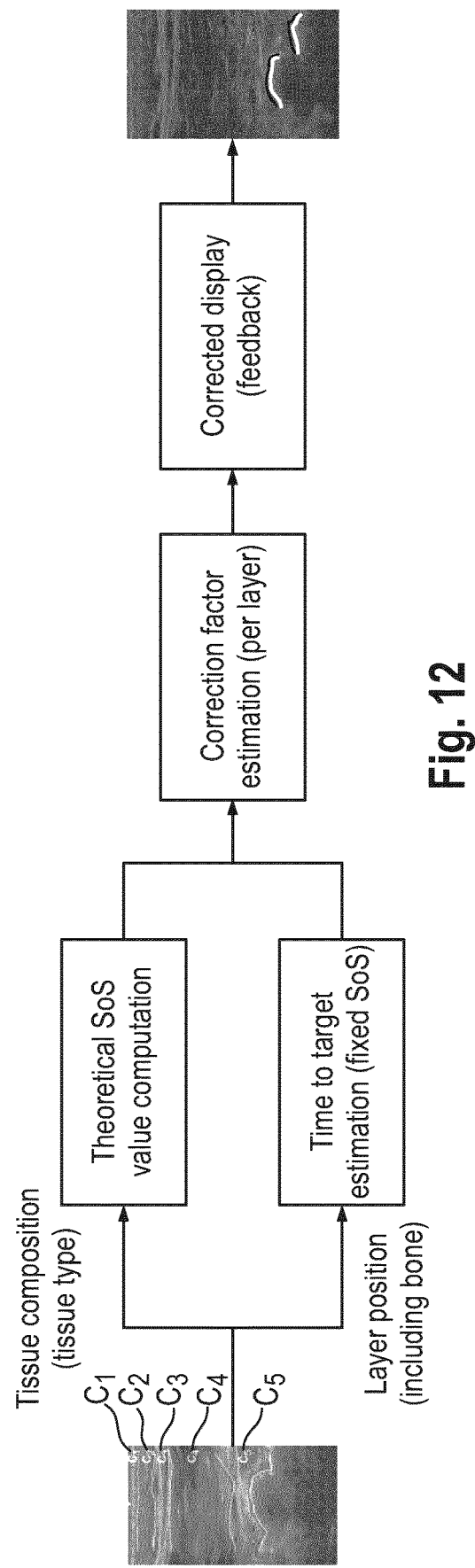
FIG. 12 shows the main steps for final bone location rectification.

FIG. 11 shows an example of tracking dynamical changes of a line profile signal extracted from the spine US images displayed in the same figure (see red line). A curvature feature is first computed as an auxiliary signal, and then an EMD decomposition is performed. Finally, a TV-AR model is computed from which the pole of maximal energy is tracked (as explained in [9]). It is possible to observe that the tracked pole jumps every sample when a transition between two different tissues occurs.

From the methods presented in sections 3.1 and 3.2 it is possible to extract for each line profile of the matrix US image two sets of parameters that are used for the final bone rectification: the position of each tissue layer including bone, and the type or structure of the tissues preceding the bone. The tissue type is used to compute the theoretical tissue-dependent speed of sound and the layer position is used to compute the average time to target using the fixed speed of sound given by the US device (see FIG. 11).

Knowing the speed of sound per tissue (for example, from literature) and the average time to target, it is possible to then compute an average distance to the bone as well as the tissue-dependent distance to the bone. Finally, a correction factor per line profile can be estimated that is used to rectify the position of the bone and reconstruct the final image where the estimated rectified version of the bone can be displayed.

A method for speed of sound calibration for rectifying the localization of bones in US images is provided. It involves three main general steps where the bone may first be detected in the US image, then tissues preceding bone may have to be identified, and finally, the rectification of the bone location may be performed by using the tissue information for computing a theoretical speed of sound that is used to perform a correction.

The method is based on a novel approach for boundary detection in images with very low signal-to-noise ratio. This approach takes the boundary problem in images not as a segmentation problem but as a space-variant dynamical change one. A dynamical change occurs on the boundary of two different textures, and the detection between textures can be achieved by tracking the dynamics (or textures in this case) in a space-texture-variant way. We showed in this work that this approach has a considerable potential to be used for speed of sound calibration.

The content of the references mentioned below is incorporated by reference.

REFERENCES

[1] D. Napolitano, C.-H. Chou, G. McLaughlin, T.-L. Ji, L. Mo, D. DeBusschere, and R. Steins, "Sound speed correction in ultrasound imaging," Ultrasonics, vol. 44, pp. e43-e46, 2006.

[2] M. S. Ziksari and B. M. Asl, "Phase aberration correction in minimum variance beamforming of ultrasound imaging," in 2015 23rd Iranian Conference on Electrical Engineering. IEEE, 2015, pp. 23-26.

[3] H.-C. Shin, R. Prager, H. Gomersall, N. Kingsbury, G. Treece, and A. Gee, "Estimation of average speed of sound using deconvolution of medical ultrasound data," Ultrasound in medicine & biology, vol. 36, no. 4, pp. 623-636, 2010.

[4] D. Pammer and E. Bognár, "Examination of bone like materials," in Materials Science Forum, vol. 812. Trans Tech Publ, 2015, pp. 233-238.

[5] I. Hacihaliloglu, "Ultrasound imaging and segmentation of bone surfaces: A review," Tech-nology, vol. 5, no. 02, pp. 74-80, 2017.

[6] A. Alsinan, M. Vives, V. Patel, and I. Hacihaliloglu, "Spine surface segmentation from ultrasound using multi-feature guided cnn," EPiC Series in Health Sciences, vol. 3, pp. 6-10, 2019.

[7] S. I. Jabbar, C. R. Day, N. Heinz, and E. K. Chadwick, "Using convolutional neural net-work for edge detection in musculoskeletal ultrasound images," in 2016 International Joint Conference on Neural Networks (IJCNN). IEEE, 2016, pp. 4619-4626.

[8] P. Fuentealba, A. Illanes, and F. Ortmeier, "Cardiotocographic signal feature extraction through ceemdan and time-varying autoregressive spectral-based analysis for fetal welfare assessment," IEEE Access, 2019.

[9] A. Illanes, A. Boese, I. Maldonado, A. Pashazadeh, A. Schaufler, N. Navab, and M. Friebe, "Novel clinical device tracking and tissue event characterization using proximally placed audio signal acquisition and processing," Scientific reports, vol. 8, no. 1, p. 12070, 2018.

Figure 13:
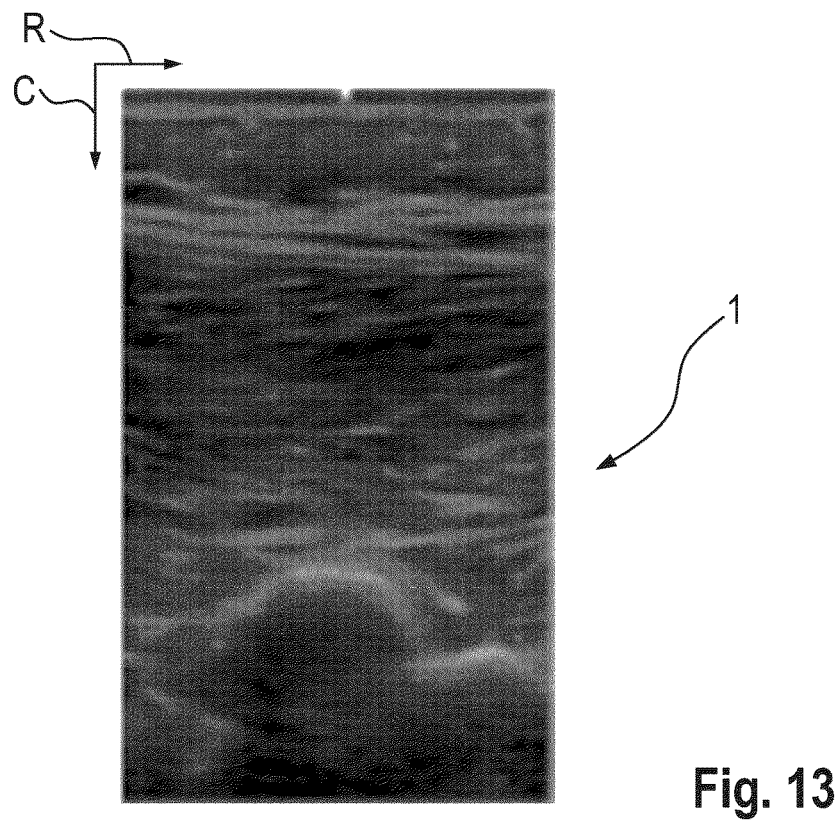
FIG. 13 shows a B-mode ultrasound image of a structured object as an example for a raster image.

The invention will be described hereinafter, in more detail and in an exemplary manner using advantageous embodiments and with reference to the figures. The described embodiments are only possible configurations in which, however, the individual features as de-scribed above can be provided independent of one another or can be omitted in the drawings:

FIG. 13 shows an exemplary embodiment of a raster image 1. As an example for a raster image 1, FIG. 13 shows a B-mode (brightness mode) image, which displays the acoustic impedance of a two-dimensional cross-section of an object, e.g. tissue in the area of the human spine. Alternatively, the raster image may be derived by other sweeping methods and/or depict other objects.

The raster image 1 comprises columns that extend along a column direction C, and rows that extend along a row direction R. Along the column and row directions C, R, pixels are arranged, which comprise image information. The value of the image information represents structural features of the object in the cross-section. For example, the values represent different brightness levels in a B-mode image.

The column direction C may represent a direction that extends away from a sweeping source. The row direction R may represent a direction that extends along the sweeping source. In the example, in which the raster image 1 is a B-mode ultrasound image, the sweeping source may be an ultrasound transducer.

Figure 14:
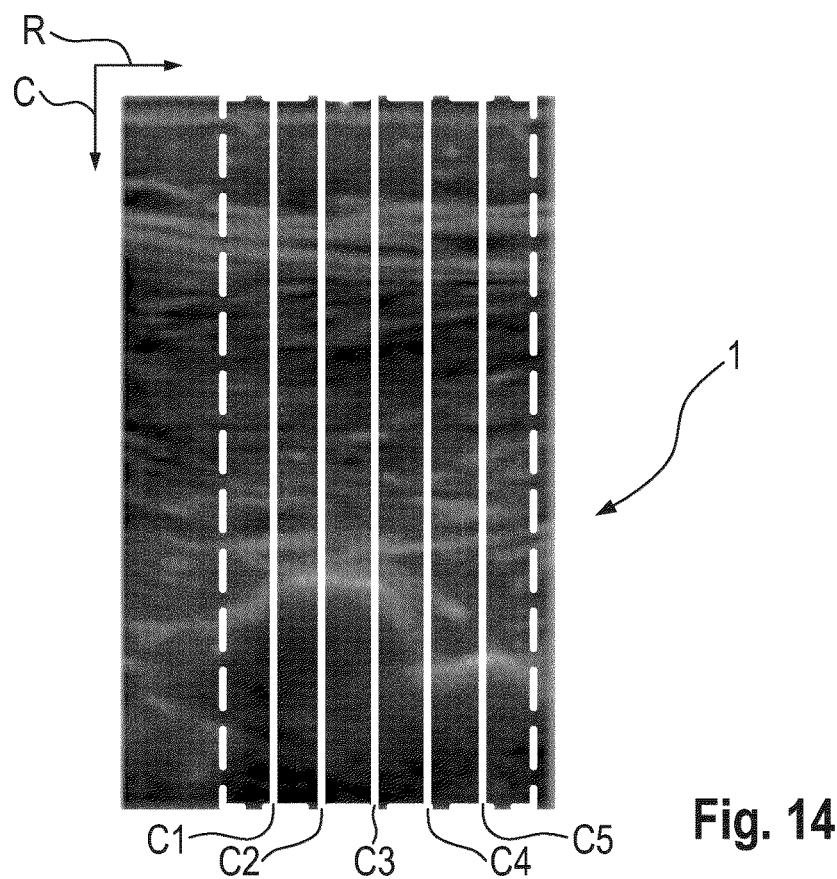
FIG. 14 shows an experimental setup involving different tissues and thicknesses for evaluating the effects of speed of sound.

FIG. 14 shows the raster image 1 of FIG. 13 with various selected pixel columns C1 to C5. The highlighting of the pixel columns C1 to C5 represents that the pixel columns C1 to C5 are selected for further investigation. More or less than five pixel columns can be selected. In particular, adjacent pixel columns or pixel columns with at least one unselected pixel column therebetween may be selected.

Figure 15:
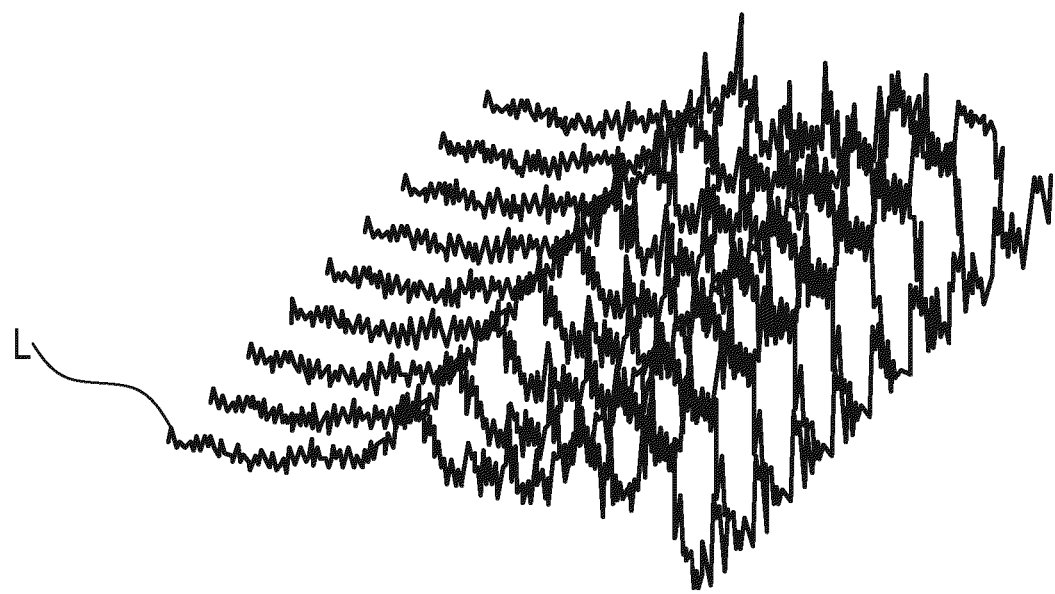
FIG. 15 shows line profiles of marled columns.

FIG. 15 depicts various line profiles L, each of which corresponding to one of the selected pixel columns C1 to C5. In the exemplary embodiment of FIG. 15, nine line profiles L are shown, such that the line profiles were derived from nine pixel columns. More or less than nine pixel columns can be selected to derive the line profiles L. The amplitude of each line profile L corresponds to the value of the image information of the pixels along the column direction C.

Figure 16:
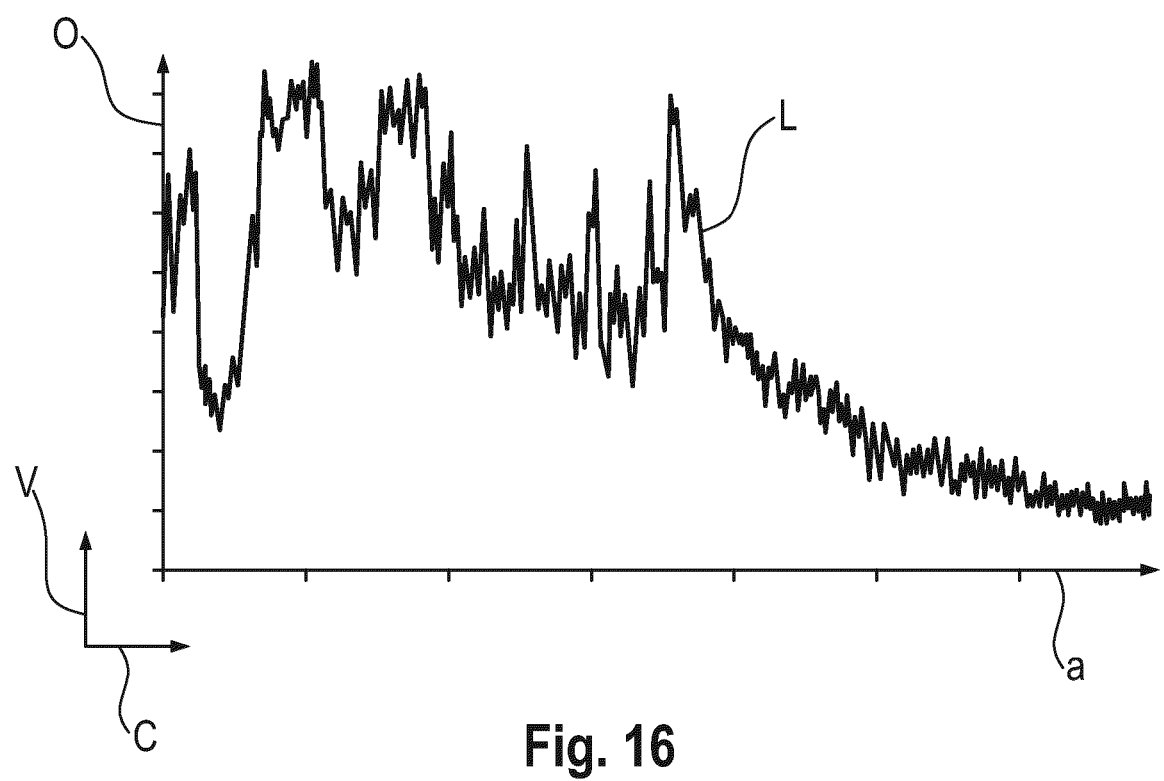
FIG. 16 shows a selected one of the line profiles.

In FIG. 16, one of the line profiles L of FIG. 15 is shown in a coordinate system. Along the abscissa a of the coordinate system, the column direction C extends. Along the ordinate o of the coordinate system, the value V of image information of the respective pixel at a respective position along the column direction C is plotted.

Figure 17:
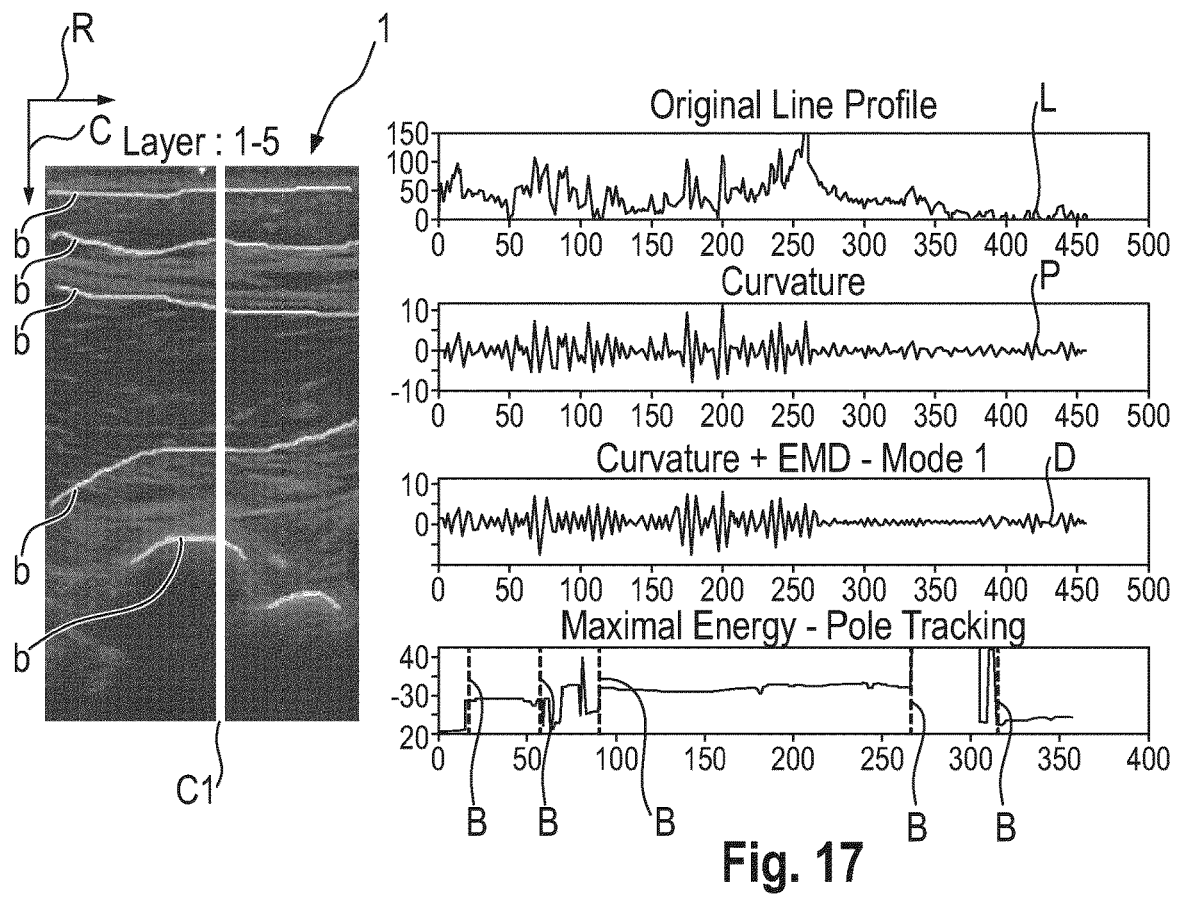
FIG. 17 shows further details of an exemplary embodiment of the method according to the invention.
Figure 19:
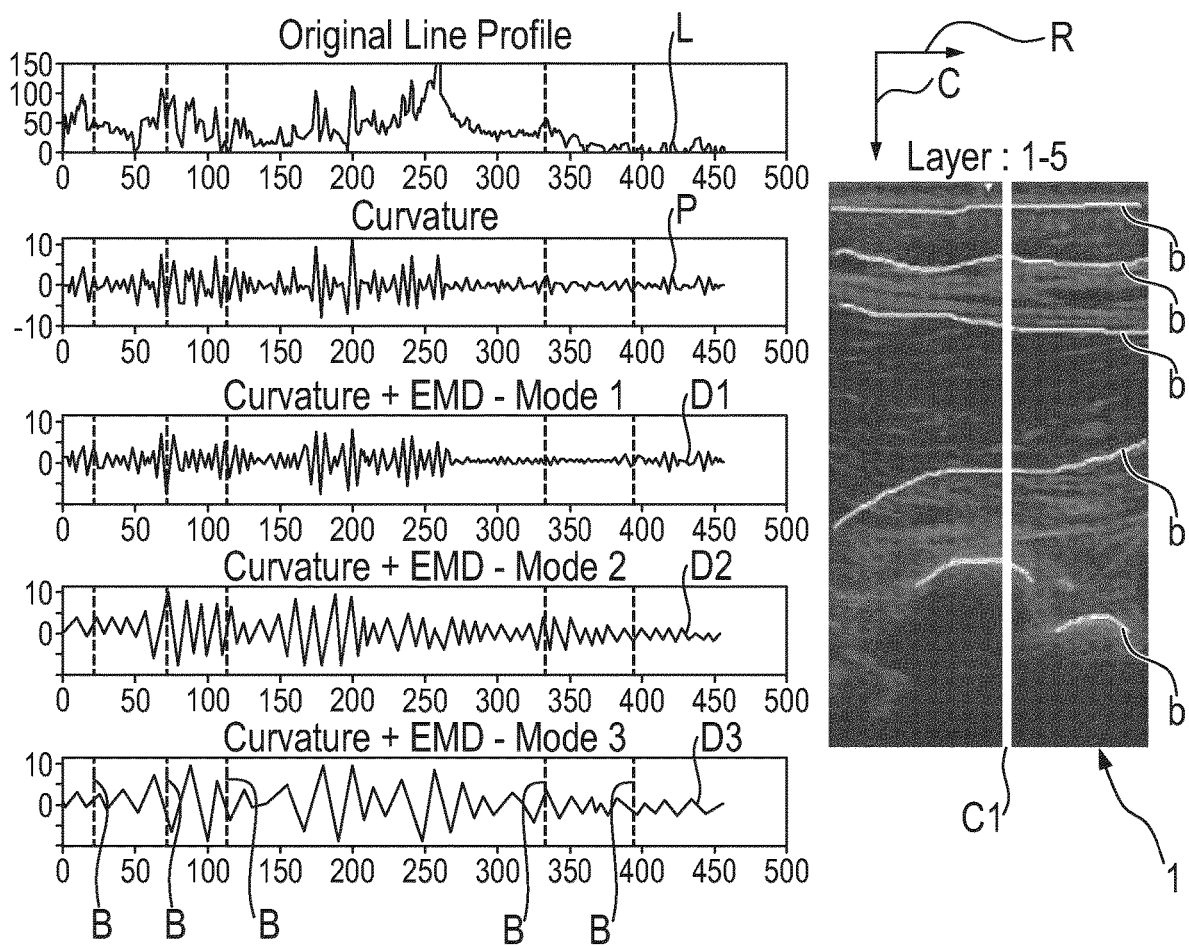
FIG. 19 shows an exemplary embodiment of the method according to the present invention.

FIGS. 17 and 19 show further details of exemplary embodiments of the method according to the invention. On the left hand side, the raster image 1 is shown as an exemplary reference. As an example for the object, the raster image 1 shows the human spine with several layers of tissue stacked one after each other along the column direction C. The tissue layers generally extend along the row direction R. The tissue layers have thicknesses that extend along the column direction C, wherein the thicknesses vary along the row direction R.

In order to characterize the object (for example spine with tissue layers) depicted in the raster image 1, for example in order to identify the object or determine its speed of sound, at least one pixel column C1 is selected and converted into a respective line profile L. After that, the line profile L may be processed to form a processed line profile P. The processed line profile P may have an enhanced signal to noise ratio compared to the selected line profile L. For example processing the selected line profile L to form a processed line profile P may comprise determining derivates, curvatures, amplitudes and/or amplitude changes of the selected line profiles. Alternatively or additionally, processing the selected line profile L to form a processed line profile P may comprise filtering the selected line profile L. In the exemplary embodiments of FIGS. 17 and 19, the curvature of the selected line profile L is determined.

Additionally, the processed line profile P may be subjected to signal decomposition to form a decomposed line profile D. For example, the method comprises decomposing the processed line profile P into n-empirical modes, wherein n is 1, 2, 3, 4 or 5 to form the decomposed line profile D. In the exemplary embodiment of FIG. 18, the curvature of the line profile L is determined.

Additionally, the processed line profile P may be subjected to signal decomposition to form a decomposed line profile D. For example, the method comprises decomposing the processed line profile P into n-empirical modes, wherein n is 1, 2, 3, 4 or 5 to form the decomposed line profile D. In the exemplary embodiment of FIG. 18, the empirical mode is 1.

In order to determine the sound speed, dynamics of the decomposed line profile may be determined by modelling the time variance or pole tracking, which may detect the maximal energy of reflections at the boundaries.

When repeating the above steps for several selected pixel columns, which may be adjacent pixel columns or may be separated by unselected pixel columns in the row direction, the boundaries B of each selected pixel column may be used to determine boundaries b between the layers and the bone in the raster image 1.

In order to determine the characteristics of the object, in the exemplary embodiments of FIGS. 17 and 19 the boundaries B between the tissue layers and the bone of the spine along the selected pixel column, dynamics of the decomposed line profile may be determined by modelling the time variance or pole tracking, which may detect the maximal energy of reflections at the boundaries. The boundaries may represent a change in the material characteristics of the object or a layer, e.g. a different tissue or bone material.

The main idea of the pole tracking shown in the figure may be that the maximal energy pole may move when the signal and fore example the ultrasound signal, passes from one tissue to another. This may happen because each tissue can involve different echogenicity dynamics representing different type of spectral distribution. The dynamics of each layer may result in different distribution of frequency components. Therefore, if the maximal energy is concerned, the location of the concentration of the spectral energy of each tissue may be meant. This may be the information that this pole provides.

When carefully considering the y-axis of the last graph of the exemplary embodiments of FIGS. 17 and 19, it may be possible to see that the energy (through the maximal energy pole) is concentrated in around 20 Hz with a stable behavior, then the pole jumps to 28 Hz (spectral energy is concentrated around 28 Hz) and also with a stable behavior. At the next segment (or tissue), the pole behaves instable with concentration of spectral energy between 21 and 40 Hz and then there is a long and stable behavior with the spectral energy located around 30 Hz. In the two las segments of the line profile the pole is stable at a high (45) frequency and then stable at a low frequency (23).

When repeating the above steps for several selected pixel columns C1 to C5, which may be adjacent pixel columns or may be separated from each other by unselected pixel columns in the row direction R, the boundaries B determined from each selected pixel column C1 to C5 may be used to determine boundaries b between the tissue and the bone material in the raster image 1.

Figure 18:
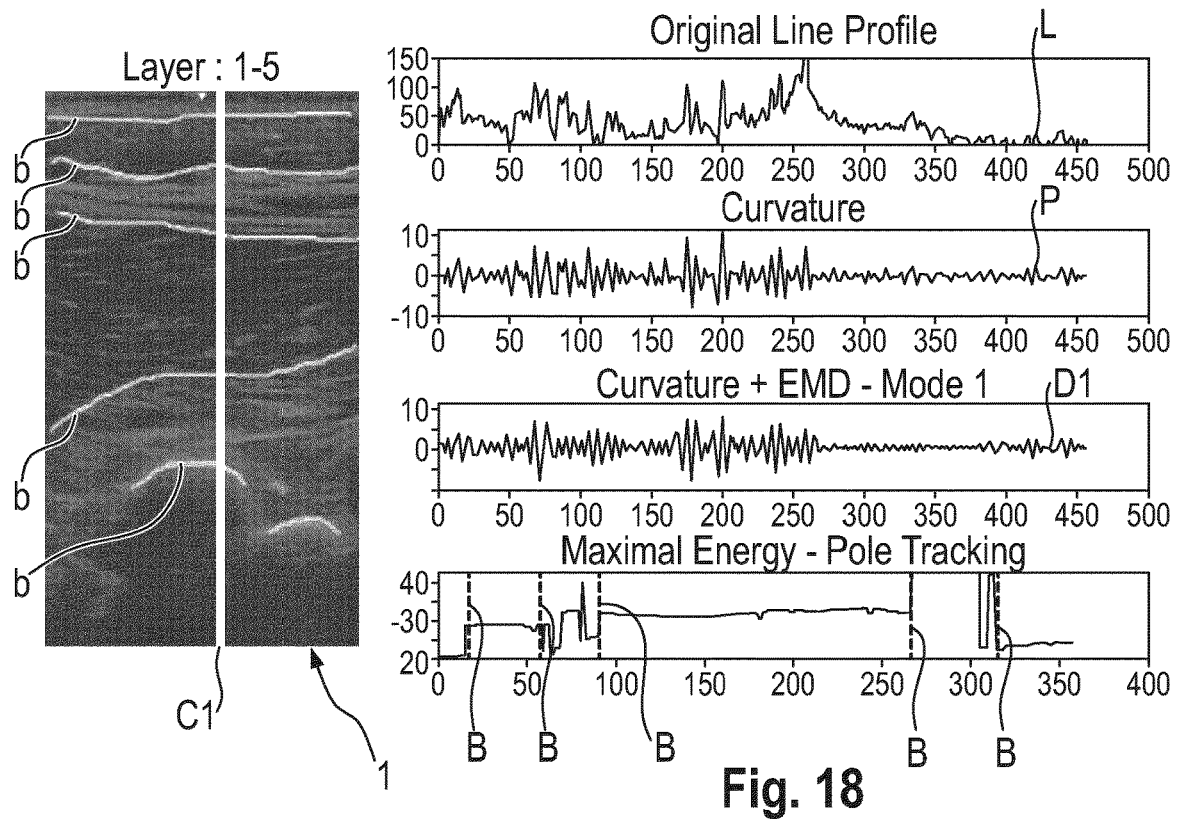
FIG. 18 shows further details of another exemplary embodiment of the method according to the invention.

FIG. 18 shows details of another exemplary embodiment of the method according to the invention.

The raster image 1 is not shown in FIG. 18, for the sake of simplicity. Again, a line profile L is derived from a pixel column, for example from selected pixel column C1. After that, the line profile L may be processed to form a processed line profile P. The processed line profile P may have an enhanced signal to noise ratio compared to the selected line profile L. For example, processing the selected line profiles to form a processed line profile may comprise applying a baseline filter to determine a baseline G. Subsequently to the determination of the baseline G, the determined baseline G may be subtracted from the line profile L to form another line E with zero crossings. The zero crossings may be used to determine the characteristics of the object. The method may continue by subjecting the line E to signal decomposition to form a decomposed line profile D. For example, the method comprises decomposing the processed line profile P into n-empirical modes, wherein n is 1, 2, 3, 4 or 5 to form the decomposed line profile D.

Figure 20:
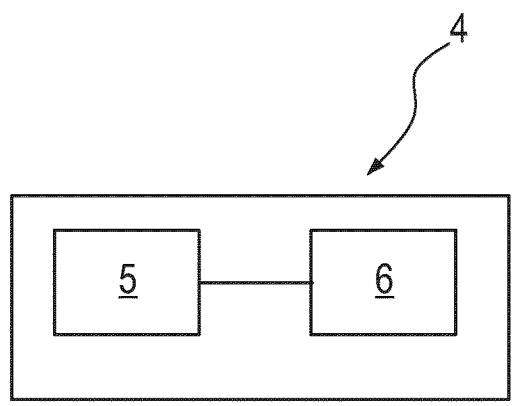
FIG. 20 is a schematic illustration of the system according to the fifth aspect.

REFERENCE NUMERALS 1 raster image
a abscissa
B, b boundary
C column direction
Cn selected pixel column
D decomposed line profile
E line with zero crossings
G baseline
L line profile
o ordinate
P processed line profile
R row direction
V value of image information FIG. 20 is a schematic illustration of the medical system 4 according to the fifth aspect. The system is in its entirety identified by reference sign 4 and comprises a computer 5 and a medical ultrasound imaging device 6. The components of the medical system 4 have the functionalities and properties explained above with regard to the fifth aspect of this disclosure.

The invention encompasses the following examples A to V:

- A. A method for identifying at least one object depicted in a raster image (1), the raster image (1) having pixel rows and pixel columns (Cn), wherein
  several pixel columns (Cn) are selected and each of the selected pixel columns (Cn) is converted into a line profile (L), the amplitude of the line profile (L) representing the value (V) of image information of selected pixels of the respective selected pixel column (Cn), wherein the method comprises
  determining characteristics of the line profiles (L) and using the characteristics to characterize the at least one object depicted in the raster image (1).
- B. The method according to example A, wherein the method comprises processing the selected line profiles (L) to form a processed line profile (P) from each of the selected line profiles (L), the processed line profiles (P) having an enhanced signal to noise ration compared to the respective selected line profile (L).
- C. The method according to example B, wherein processing the selected line profiles (L) to form a processed line profile (P) comprises
  determining individual offset values for selected amplitudes of selected line profiles (L) and subtracting the individual offset values from the respective amplitude prior to determining the characteristics of the line profiles (L) to create the processed line profile (P, E).
- D. The method according to example C, wherein the characteristic of the selected line profiles (L) are zero crossings of the processed line profiles (P, E).
- E. The method according to example C or D, wherein the method comprises determining different aspects of the processed line profile (P, E) by performing signal decomposition of the processed line profile (P, E).
- F. The method according to any of claims C to E, wherein the method comprises determining dynamics of the processed line profile (P, E).
- G. The method according to example F, wherein the method comprises deriving space variant information from the determined dynamics of the processed line profile (P, E).
- H. The method according to any of example C to G, wherein the method comprises
  detecting dynamical changes in the processed line profile (P, E).
- I. The method according to example H, wherein the method comprises providing pre-known candidates for the at least one object and comparing dynamical change data of the pre-known candidates with the detected dynamical changes.
- J. The method according to example H or I, wherein the method comprises performing selected steps of the steps of examples A to G and selected steps of the steps of example H or I for selected of the line profiles (L) and determine the consistency of the detected dynamical changes over the selected line profiles (L).
- K. The method according to example J, wherein the method comprises applying an artificial intelligence for comparing the dynamical change data with the detected dynamical changes.
- L. The method according to claim J or K, wherein the method comprises applying an artificial intelligence for determining the consistency of the detected dynamical changes over the selected line profiles (L).
- M. The method according to any of examples J to L, wherein the method comprises
  setting a boundary (B) of the at least one object as the identifying feature of the at least one object based on detected dynamical changes with a consistency higher than a pre-defined value.
- N. The method according to example M, wherein the method comprises
  identifying boundaries (b) of several different objects depicted in the raster image (1).
- O. The method according to any of claims A to N, wherein the raster image (1) is a B-mode ultrasound image.
- P. Device for identifying at least one object depicted in a raster image (1), the raster image (19 having pixel rows and pixel columns, wherein the device is adapted to perform the method of examples A to O.
- Q. A method for determining the speed of sound in a multilayer object comprising layers of known materials and sequence, but with unknown layer thicknesses, comprising the steps of
  selecting a B-mode image (1) of a cross section of the multilayer object, the B-mode image (1) being created by
  introducing the sound into the object,
  receiving a reflected sound, the reflected sound being formed by
  reflecting the introduced sound at the boundaries (b) of the layers, and
  creating the B-mode image (1) of the cross section of the layers based on the reflected sound, the B-mode image (1) being a raster image, the raster image having pixel rows and pixel columns, and
  estimating the layers and their material based on their sequence in the B-mode image (1), wherein
  several pixel columns (Cn) are selected and each of the selected pixel columns (Cn) is converted into a line profile (L), the amplitude of the line profile (L) representing the value (V) of image information of selected pixels of the respective selected pixel column (Cn), wherein the method comprises
  determining characteristics of the line profiles (L) and using the characteristics determine the speed of sound in at least one of the layers.
- R. The method according to example P, wherein the method comprises processing the selected line profiles (L) to form a processed line profile (P) from each of the selected line profiles (L), the processed line profiles (P) having an enhanced signal to noise ration compared to the respective selected line profile (L).

S. The method according to example R, wherein processing the selected line profiles (L) to form processed line profiles (P) comprises
calculating the curvature of the respective selected line profile (L).

T The method according to example R or S, wherein the method comprises
decomposing the processed line profile (P) into n-empirical modes, wherein n is 1, 2, 3, 4 or 5 to form a decomposed line profile (Dn).

U. The method according to example T, wherein the method comprises
determining different frequency changes in time as a result from the changes in structure at the boundaries (b) from the decomposed line profile (Dn) by pole-tracking.

V. Device for determining the speed of sound in a multilayer object comprising layers of known materials and sequence, but with unknown layer thicknesses, from a B-mode image (1) of the object, the B-mode image (1) having pixel rows and pixel columns, wherein the device is adapted to perform the method of example Q to U.

The invention claimed is:

1. A method for characterizing at least one object depicted in a raster image, the raster image being an ultrasound image having pixel rows and pixel columns,
wherein at least one pixel column is selected and the at least one pixel column selected is converted into a selected line profile, an amplitude of the selected line profile representing a value of image information of selected pixels of the at least one pixel column selected, and
wherein the method comprises:
determining characteristics of the selected line profile and using the characteristics to characterize the at least one object depicted in the raster image, wherein the characteristics of the selected line profile are values of the selected line profile indicating the position of an edge of the at least one object, among values of the selected line profile, with a greatest distance from a predetermined position and having a predetermined relationship to a threshold value; and
processing the selected line profile to form a processed line profile, the processed line profile having an enhanced signal to noise ratio compared to the respective selected line profile, wherein processing the selected line profile to form the processed line profile includes determining individual offset values for selected amplitudes of the selected line profile and subtracting the individual offset values from respective amplitudes prior to determining the characteristics of the selected line profile to create the processed line profile,
wherein the predetermined relationship includes zero crossings of the processed line profile.

2. The method of claim 1, further comprising determining different aspects of the processed line profile by performing signal decomposition of the processed line profile.

3. The method of claim 1, further comprising identifying boundaries of a plurality of different objects depicted in the raster image.

4. The method of claim 1, wherein the raster image is a B-mode ultrasound image.

5. The method of claim 1, wherein processing the selected line profile to form the processed line profile includes calculating the curvature of the selected line profile.

6. The method of claim 1, further comprising decomposing the processed line profile into n-empirical modes, wherein n is one of 1, 2, 3, 4 or 5, to form a decomposed line profile.

7. The method of claim 6, further comprising determining different frequency changes in time as a result from changes in structure at boundaries from the decomposed line profile by pole-tracking.

8. A non-transitory, computer-readable storage medium having stored thereon computer-executable instructions that, when executed by at least one processor, configure the at least one processor to carry out the method of claim 1.

9. A medical system, comprising:
at least one computer having at least one processor; and
a medical ultrasound imaging device for carrying out ultrasound imaging on a patient,
wherein the at least one computer is operably coupled to the medical ultrasound imaging device for receiving a signal from the medical ultrasound imaging device corresponding to a raster image having pixel rows and pixel columns, wherein at least one pixel column is selected and the at least one pixel column selected is converted into a selected line profile, an amplitude of the selected line profile representing a value of image information of selected pixels of the at least one pixel column selected, the at least one processor being configured to:
determine characteristics of the selected line profile and using the characteristics to characterize the at least one object depicted in the raster image, wherein the characteristics of the selected line profile are values of the selected line profile indicating the position of an edge of the at least one object, among values of the selected line profile, with a greatest distance from a predetermined position and having a predetermined relationship to a threshold value; and
processing the selected line profile to form a processed line profile, the processed line profile having an enhanced signal to noise ratio compared to the selected line profile, wherein processing the selecting line profile to form the processed line profile includes determining individual offset values for selected amplitudes of the selected line profile and subtracting the individual offset values from respective amplitudes prior to determining the characteristics of the selected line profile to create the processed line profile,
wherein the predetermined relationship includes zero crossings of the processed line profile.

* * * * *